(12) United States Patent
Mogna et al.

(10) Patent No.: US 10,286,017 B2
(45) Date of Patent: May 14, 2019

(54) PROBIOTIC BACTERIAL STRAINS AND SYMBIOTIC COMPOSITION CONTAINING THE SAME INTENDED FOR INFANT FOOD

(75) Inventors: Giovanni Mogna, Novara (IT); Gian Paolo Strozzi, Novara (IT); Luca Mogna, Novara (IT)

(73) Assignee: PROBIOTICAL S.P.A., Novara (NO) (IT)

( * ) Notice: Subject to any disclaimer, the term of this patent is extended or adjusted under 35 U.S.C. 154(b) by 39 days.

(21) Appl. No.: 14/116,999

(22) PCT Filed: May 9, 2012

(86) PCT No.: PCT/IB2012/000897
§ 371 (c)(1),
(2), (4) Date: Dec. 20, 2013

(87) PCT Pub. No.: WO2013/050833
PCT Pub. Date: Apr. 11, 2013

(65) Prior Publication Data
US 2014/0093479 A1    Apr. 3, 2014

(30) Foreign Application Priority Data
May 9, 2011   (IT) .................... MI2011A0793

(51) Int. Cl.
| | |
|---|---|
| *A61K 35/745* | (2015.01) |
| *C12R 1/01* | (2006.01) |
| *A23L 33/135* | (2016.01) |
| *A61K 35/74* | (2015.01) |

(52) U.S. Cl.
CPC .......... *A61K 35/745* (2013.01); *A23L 33/135* (2016.08); *C12R 1/01* (2013.01); *A61K 35/74* (2013.01)

(58) Field of Classification Search
None
See application file for complete search history.

(56) References Cited

U.S. PATENT DOCUMENTS

| | | |
|---|---|---|
| 3,819,383 A | 6/1974 | Squire et al. |
| 3,819,838 A | 6/1974 | Smith et al. |
| 4,187,321 A | 2/1980 | Mutai |
| 4,332,790 A | 6/1982 | Sozzi et al. |
| 4,670,272 A | 6/1987 | Chen et al. |
| 4,853,211 A | 8/1989 | Kurobe et al. |
| 5,071,976 A | 12/1991 | Stirling |
| 5,343,672 A | 9/1994 | Kearney et al. |
| 5,413,960 A | 5/1995 | Dobrogosz et al. |

(Continued)

FOREIGN PATENT DOCUMENTS

| | | |
|---|---|---|
| CA | 2221426 | 5/1998 |
| CA | 2739345 | 4/2010 |

(Continued)

OTHER PUBLICATIONS

Del Piano et al., J. Clin. Gastroenterol. 44: S42-S46 (2010).*

(Continued)

*Primary Examiner* — Erin M. Bowers
(74) *Attorney, Agent, or Firm* — Steinfl + Bruno LLP

(57) ABSTRACT

Selection of probiotic strains belonging to the genus *Bifidobacterium* and to a symbiotic composition containing the same for use of feeding infants, is described.

9 Claims, 3 Drawing Sheets

Listeria monocytogenes ATCC 19112

(56) References Cited

U.S. PATENT DOCUMENTS

| | | |
|---|---|---|
| 5,466,463 A | 11/1995 | Ford |
| 6,262,019 B1 | 7/2001 | Keller et al. |
| 6,277,370 B1 | 8/2001 | Vesely et al. |
| 6,706,347 B1 | 3/2004 | Kurzinger et al. |
| 8,257,693 B2 | 9/2012 | Ranganathan |
| 9,005,682 B2 * | 4/2015 | Sprenger ............... A23C 9/1425 424/93.4 |
| 9,125,768 B2 | 9/2015 | Husmark et al. |
| 9,492,377 B2 | 11/2016 | Mogna et al. |
| 9,883,692 B2 | 2/2018 | Hougee et al. |
| 9,925,224 B2 | 3/2018 | Mogna et al. |
| 2002/0022019 A1 | 2/2002 | Laulund |
| 2002/0044968 A1 | 4/2002 | Van Lengerich |
| 2004/0185032 A1 * | 9/2004 | Burrell ................ A61K 31/135 424/93.45 |
| 2004/0208863 A1 | 10/2004 | Versalovic et al. |
| 2005/0017013 A1 | 1/2005 | Peisach et al. |
| 2005/0031814 A1 | 2/2005 | Dawes |
| 2005/0095232 A1 | 5/2005 | Volkmann |
| 2006/0039973 A1 | 2/2006 | Aldritt et al. |
| 2006/0121571 A1 | 6/2006 | Klaenhammer |
| 2006/0233774 A1 | 10/2006 | Lim et al. |
| 2007/0122397 A1 | 5/2007 | Sanguansri et al. |
| 2007/0148149 A1 | 6/2007 | Boettner et al. |
| 2007/0207132 A1 * | 9/2007 | Speelmans ............. A23L 1/296 424/93.45 |
| 2007/0269515 A1 | 11/2007 | Henriksen |
| 2008/0175899 A1 | 7/2008 | Ross et al. |
| 2008/0187628 A1 | 8/2008 | Champion |
| 2008/0193485 A1 | 8/2008 | Gorbach et al. |
| 2009/0041736 A1 | 2/2009 | Sprenger et al. |
| 2009/0061164 A1 | 3/2009 | Pasbrig et al. |
| 2009/0170185 A1 | 7/2009 | Hayakawa et al. |
| 2009/0175843 A1 | 7/2009 | Gans |
| 2009/0226548 A1 | 9/2009 | Minatelli et al. |
| 2009/0252709 A1 | 10/2009 | Nose et al. |
| 2009/0294319 A1 | 12/2009 | Nageli et al. |
| 2010/0003369 A1 | 1/2010 | Ter Haar et al. |
| 2010/0092440 A1 | 4/2010 | Strozzi et al. |
| 2011/0020400 A1 | 1/2011 | MacSharry et al. |
| 2011/0177198 A1 | 7/2011 | Songisepp et al. |
| 2011/0178488 A1 | 7/2011 | Balazs |
| 2012/0195868 A1 | 8/2012 | Lathan et al. |
| 2012/0207929 A1 | 8/2012 | Yoo et al. |
| 2014/0065116 A1 | 3/2014 | Mogna et al. |
| 2014/0072543 A1 | 3/2014 | Mogna |
| 2014/0105874 A1 | 4/2014 | Mogna et al. |
| 2014/0127164 A1 | 5/2014 | Mogna et al. |
| 2014/0231300 A1 | 8/2014 | Mogna |
| 2014/0328932 A1 | 11/2014 | Mogna |
| 2015/0017128 A1 | 1/2015 | Mogna |
| 2016/0106787 A1 | 4/2016 | Mogna |
| 2016/0184372 A1 | 6/2016 | Mogna |
| 2017/0014335 A1 | 1/2017 | Mogna et al. |

FOREIGN PATENT DOCUMENTS

| | | |
|---|---|---|
| CN | 1233474 A | 11/1999 |
| CN | 1345589 A | 4/2002 |
| CN | 1853508 A | 11/2006 |
| CN | 101432007 A | 5/2009 |
| CN | 101801220 A | 8/2010 |
| CN | 105163747 A | 12/2015 |
| EA | 200200287 A1 | 6/2002 |
| EA | 011952 | 9/2004 |
| EA | 010981 | 2/2007 |
| EP | 0002692 | 7/1979 |
| EP | 0845350 | 6/1998 |
| EP | 0956858 | 11/1999 |
| EP | 1600060 | 11/2005 |
| EP | 1600061 | 11/2005 |
| EP | 1840205 A1 | 10/2007 |
| EP | 2000530 A1 | 12/2008 |
| EP | 2210505 A1 | 7/2010 |
| EP | 2269465 A1 | 1/2011 |
| EP | 2338976 A1 | 6/2011 |
| EP | 2360237 A1 | 8/2011 |
| EP | 2626076 A1 | 8/2013 |
| JP | 2011-258549 A | 9/2001 |
| JP | 2003522731 A | 7/2003 |
| JP | 2006-519014 A | 8/2006 |
| JP | 2008-529535 A | 8/2008 |
| JP | 2009-520470 A | 5/2009 |
| JP | 2010-511033 A2 | 4/2010 |
| JP | 2010511033 A | 4/2010 |
| JP | 2010-187670 A | 9/2010 |
| JP | 2013009681 A | 1/2013 |
| KZ | 11784 | 8/2002 |
| KZ | 17967 | 6/2011 |
| RU | 02150268 | 6/2000 |
| RU | 2203946 C1 | 5/2003 |
| RU | 2215656 C2 | 11/2003 |
| RU | 2303058 C2 | 7/2007 |
| RU | 2338511 C2 | 11/2008 |
| RU | 2007147945 A | 7/2009 |
| RU | 2373274 C1 | 11/2009 |
| RU | 2008118418 A | 11/2009 |
| RU | 2388479 C1 | 5/2010 |
| WO | 94/12142 | 6/1994 |
| WO | 97/29762 A1 | 8/1997 |
| WO | 99/49877 | 10/1999 |
| WO | 0035465 A2 | 6/2000 |
| WO | 00/72855 | 12/2000 |
| WO | 03090546 A1 | 11/2003 |
| WO | 2004/089278 | 10/2004 |
| WO | 2004/101770 | 11/2004 |
| WO | 2006/013588 A1 | 2/2006 |
| WO | 2006/073329 A1 | 7/2006 |
| WO | 2006/091103 A2 | 8/2006 |
| WO | 2007/029773 A1 | 3/2007 |
| WO | 2007/100765 | 9/2007 |
| WO | 2001/125558 | 11/2007 |
| WO | 2008/038075 | 4/2008 |
| WO | 2008/065492 | 6/2008 |
| WO | WO 2008/153377 | * 12/2008 |
| WO | WO 2008/153377 A1 | * 12/2008 |
| WO | 2009/138218 | 11/2009 |
| WO | 2010/023248 | 3/2010 |
| WO | 2010/033768 A1 | 3/2010 |
| WO | 2010/099824 | 9/2010 |
| WO | 2010/103374 | 9/2010 |
| WO | 2010/9099824 | 9/2010 |
| WO | 2010/133761 A1 | 11/2010 |
| WO | 2011/012932 | 2/2011 |
| WO | 2011/017040 | 2/2011 |
| WO | 2011/110918 A1 | 9/2011 |
| WO | 2012/001440 | 1/2012 |
| WO | 2012/101500 A1 | 8/2012 |
| WO | 2010/136891 A1 | 3/2013 |
| WO | 2013/034974 | 3/2013 |
| WO | 2013/034975 A1 | 3/2013 |
| WO | 2013/050831 A1 | 4/2013 |

OTHER PUBLICATIONS

Grimoud et al., Anaerobe 16: 493-500 (2010).*
Puccio et al., Nutrition 23: 1-8 (2007).*
Ouwehand et al., Antonie van Leeuwenhoek 82: 279-289 (2002).*
Scardovi et al., Int. J. Syst. Bacteriol. 29(4): 312-327 (1979).*
First Office Action dated Nov. 4, 2014 for Chinese Patent Application No. 201280022854.9 filed on May 9, 2012 in the name of Probiotical S.P.A. (English + Chinese).
Final Office Action dated Dec. 30, 2014 U.S. Appl. No. 14/005,821, filed Nov. 6, 2013 in the name of Giovanni Mogna.
Restriction Requirement dated Feb. 20, 2015 U.S. Appl. No. 14/117,003, filed Dec. 27, 2013 in the name of Giovanni Mogna.
Restriction Requirement dated Feb. 4, 2015 U.S. Appl. No. 14/116,996, filed Dec. 18, 2013 in the name of Giovanni Mogna.
Non-Final Office Action dated Mar. 10, 2015 for U.S. Appl. No. 13/982,255, filed Nov. 12, 2013 in the name of Giovanni Mogna.

(56) References Cited

OTHER PUBLICATIONS

Ronnqvist, D. et al. "*Lactobacillus fermentum* Ess-1 with unique growth inhibition of vulva-vaginal candidiasis pathogens" Journal of Medical Microbiology (2007), 56, pp. 1500-1504.
PCT International Search Report dated Sep. 21, 2012 for PCT/IB2012/000895 filed on May 9, 2013 in the name of Probiotical S.P.A.
PCT Written Opinion dated Sep. 21, 2012 for PCT/IB2012/000895 filed on May 9, 2013 in the name of Probiotical S.P.A.
PCT International Search Report dated Sep. 27, 2012 for PCT/IB2012/000907 filed on May 9, 2013 in the name of Probiotical S.P.A.
PCT Written Opinion dated Sep. 27, 2012 for PCT/IB2012/000907 filed on May 9, 2013 in the name of Probiotical S.P.A.
PCT International Search Report dated Aug. 24, 2012 for PCT/IB2012/000897 filed on May 9, 2013 in the name of Probiotical S.P.A.
PCT Written Opinion dated Aug. 24, 2012 for PCT/IB2012/000897 filed on May 9, 2013 in the name of Probiotical S.P.A.
Modesto, M. et al. *Resistant to freezing and freeze-drying storage processes of potential probiotic bifidobacteria*. Annals of Microbiology, 54 (1), pp. 43-48 (2004).
Likotrafiti, E. et al. *Molecular Identification and Anti-pathogenic Activities of Putative Probiotic Bacteria Isolated from Faeces of Healthy Elderly Individuals*. Microbial Ecology in Health and Disease, 16, pp. 105-112 (2004).
A. Amaretti, et al. "Antioxidant properties of potentially probiotic bacteria: in vitro and in vivo activities", Applied Microbiology and Biotechnology. vol. 97 (2), 2013, pp. 809-817.
C P Champagne, et al: "The determination of viable counts in probiotic cultures microencapsulated by spray-coating", Food Microbiology, Academic Press LTD, London, GB, vol. 27, No. 8, Dec. 1, 2010 (Dec. 1, 2010), pp. 1104-1111. Abstract Only.
M.C. Collado, et al: "Probiotic Strains and Their Combination Inhibit in Vitro Adhesion of Pathogens to Pig Intestinal Mucosa", Current Microbiology, Springer-Verlag, NE, vol. 55, No. 3, Jul. 25, 2007 (Jul. 25, 2007), pp. 260-265. Abstract Only.
M. Del Piano, et al: "Is microencapsulation the future of probiotic preparations? The increased efficacy of gastro-protected probiotics", Gut Microbes Mar.-Apr. 2011 LNKDPUBMED: 21637030, vol. 2, No. 2, Mar. 2011 (Mar. 2011), pp. 120-123.
K.A. Eaton, et al: "Probiotic *Lactobacillus reuteri* Ameliorates Disease Due to Enterohemorrhagic *Escherichia coli* in Germfree Mice", Infection and Immunity, vol. 79, No. 1, Oct. 25, 2010 (Oct. 25, 2010), pp. 185-191.
European Commission Health & Consumer Protection Directorate-General, "Opinion of the Scientific Committee on Animal Nutrition on the Criteria for Assessing the Safety of Micro-organisms Resistant to Antibiotics of Human Clinical and Veterinary Importance", (Revised 2002) 20 pages.
European Food Safety Authority, "Opinion of the Scientific Panel on Additives and Products or Substances used in Animal Feed on the updating of the criteria used in the assessment of bacteria for resistance to antibodies of human or veterinary importance", The EFSA Journal (2005) 223, 1-12.
M.F. Fernandez, et al: "Probiotic properties of human lactobacilli strains to be used in the gastrointestinal tract", Journal of Applied Microbiology, Oxford, GB, vol. 94, No. 3, Online Feb. 12, 2003, pp. 449-455.
FAO/WHO. *Guidelines for the Evaluation of Probiotics in Food*. Apr. 30/May 1, 2002, 11 pgs.
M. Gotteland, et al, "Systematic review: are probiotics useful in controlling gastric colonization by *Helicobacter pylori*?" Alimentary Pharmacology & Therapeutics, vol. 23, pp. 1077-1086, Apr. 15, 2006.
M Gueimonde, et al: "Adhesion and competitive inhibition and displacement of human enteropathogens by selected lactobacilli", Food Research International, Elsevier Applied Science, Barking, GB, vol. 39, No. 4, May 1, 2006 (May 1, 2006), pp. 467-471. Summary Citation.

P Hütt, et al: "Antagonistic activity of probioitic lactobacilli and bifidobacteria aganst entero- and uropathogens", Journal of Applied Microbiology, vol. 100, No. 6, Jun. 2006 (Jun. 2006), pp. 1324-1332.
H.Q. Huynh, et al: "N-Acetylcysteine, a Novel Treatment for *Helicobacter pylori* Infection", Digestive Diseases and Sciences, Kluwer Academic Publishers-Plenum Publishers, NE, vol. 49, No. 11-12, Nov. 1, 2004 (Nov. 1, 2004), pp. 1853-1861.
K.C. Johnson-Henry, et al: "*Lactobacillus rhamnosus* Strain GG Prevents Enterohemorrhagic *Escherichia coli* O157:H7-Induced Changes in Epithelial Barrier Function", Infection and Immunity, vol. 76, No. 4, Apr. 1, 2008 (Apr. 1, 2008), pp. 1340-1348.
M.A. Losada, et al. "Towards a healthier diet for the colon: the influence of fructooligosaccharides and lactobacilli on intestinal health", Nutrition Research, vol. 22, Jan. 2002, pp. 71-84.
Hong Lu, et al: "New development in the mechanistic understanding of peptic ulcer diseases", Drug Discovery Today: Disease Mechanisms, Elsevier, vol. 3, No. 4, 2006, pp. 431-437.
F. Lutgendorff, et al., "Probiotics enhance pancreatic glutathione biosynthesis and reduce oxidative stress in experimental acute pancreatitis", Am. J. Physiol. Gastrointest. Liver Physiol., 2008, vol. 295; G1111-G1121.
M. Malecka, "Antioxidant properties of the unsaponifiable matter isolated from tomato seeds, oat grains and wheat germ oil" Food Chemistry, 2002, vol. 79, pp. 327-330.
A Marchese, et al.: "Effect of fosfomycin alone and in combination with N-acetylcysteine on *E. coli* biofilms", International Journal of Antimicrobial Agents, vol. 22, Oct. 1, 2003, Suppl. 2, (Oct. 1, 2003), pp. 95-100.
L.V. McFarland: "Meta-analysis of probiotics for the prevention of antibiotic associated diarrhea and the treatment of *Clostridium difficile* disease", The American Journal of Gastroenterology Apr. 2006 LNKD-PUBMED:16635227, vol. 101, No. 4, Apr. 2006 (Apr. 2006), pp. 812-822.
L. Ouoba, et al., "Resistance of potential lactic acid bacteria and bifidobacteria of African and European origin to antimicrobials: Determination and transferability of the resistance genes to other bacteria", International Journal of Food Microbiology (2008) 121, 217-224.
D. Infante Pina, et al., "Prevalence and dietetic management of mild gastrointestinal disorders in milk-fed infants", World Journal of Gastroenterology, 2008, vol. 14, No. 2: 248-254.
V. Rada, et al: "Susceptibility of bifidobacteria to lysozyme as a possible selection criterion for probiotic bifidobacterial strains", Biotechnology Letters, Springer Netherlands, Dordrecht, vol. 32, No. 3, Nov. 27, 2009 (Nov. 27, 2009), pp. 451-455. Abstract Only.
V. Rada, et al. "Susceptibility of bifidobacteria to nisin", Letters in Applied Microbiology, vol. 26, 1998, pp. 123-125.
C. Santini et al., "Characterization of probiotic strains: an application as feed additives in poultry against *Campylobacter jejuni*", Int J Food Microbiol., 2010, 141 Suppl 1:S98-108. Epub Apr. 8, 2010. Abstract Only.
S. Torriani, et al. "Differentiation of *Lactobacillus plantarum*, *L. pentosus*, and *L. paraplantarum* by recA Gene Sequence Analysis and Multiplex PCR Assay with recA Gene-Derived Primers", Appl. Environ. Microbiol. 2001. vol. 67 (8), pp. 3450-3454.
J. Walter, et al. "Detection and Identification of Gastrointestinal *Lactobacillus* Species by Using Denaturing Gradient Gel Electrophoresis and Species-Specific PCR Primers", Appl. Environ. Microbiol. 2000. vol. 66 (1), pp. 297-303.
Dan Yang Ying, et al: "Microencapsulated Lactobacillus rhamnosus GG Powders: Relationship of Powder Physical Properties to Probiotic Survival during Storage", Journal of Food Science, vol. 75, No. 9, Nov. 1, 2010 (Nov. 1, 2010), pp. E588-E595. Abstract Only.
L. Zhang, et al., "Evaluation of Lactobacillus rhamnosus GG using an *Escherichia coli* K88 model of piglet diarrhoea: Effects on diarrhoea incidence, faecal microflora and immune responses", Veterinary Microbiology, Elsevier BV. NL, vol. 141, No. 1-2, Feb. 24, 2010, pp. 142-148. Epub Sep. 11, 2009. Abstract Only.
International Search Report dated Dec. 3, 2012 for PCT/IB2012/001741 filed on Sep. 10, 2012 in the name of Giovanni Mogna.
Written Opinion dated Dec. 3, 2012 for PCT/IB2012/001741 filed on Sep. 10, 2012 in the name of Giovanni Mogna.

(56) References Cited

OTHER PUBLICATIONS

PCT International Search Report dated Dec. 17, 2012 for PCT/IB2012/001745 filed on Sep. 10, 2012 in the name of Probiotical S.p.A.
Written Opinion dated Dec. 17, 2012 for PCT/IB2012/001745 filed on Sep. 10, 2012 in the name of Probiotical S.P.A.
International Search Report dated Dec. 3, 2012 for International patent application PCT/IB2012/001848 filed on Sep. 21, 2012 in the name of Probiotical S.P.A.
International Written Opinion dated Dec. 3, 2012 for International patent application PCT/IB2012/001848 filed on Sep. 21, 2012 in the name of Probiotical S.P.A.
Search Report dated Nov. 11, 2011 for IT MI20110792 filed on May 9, 2011 in the name of Probiotical S.P.A.
Written Opinion dated Nov. 11, 2011 for IT MI20110792 filed on May 9, 2011 in the name of Probiotical S.P.A.
First Examination Report dated Apr. 28, 2014 for NZ IP No. 614002 filed on Aug. 6, 2013 in the name of Probiotical S.P.A.
Office Action dated Jul. 15, 2014 for KZ Application No. 2013/1615.1 filed on Jan. 24, 2012 by Tagbergenova Alma Taishevna et al.
Restriction Requirement dated Jan. 7, 2014 for U.S. Appl. No. 14/005,821, filed Nov. 6, 2013.
Non-Final Office Action dated Jun. 5, 2014 for U.S. Appl. No. 14/005,821, filed Nov. 6, 2013.
Restriction Requirement dated Oct. 17, 2014 for U.S. Appl. No. 13/982,255, filed Nov. 12, 2013.
PCT International Preliminary Report on Patentability dated Nov. 12, 2013 for PCT/IB2012/000895 filed on May 9, 2013 in the name of Probiotical S.P.A.
PCT International Preliminary Report on Patentability dated Nov. 12, 2013 for PCT/IB2012/000897 filed on May 9, 2013 in the name of Probiotical S.P.A.
PCT International Preliminary Report on Patentability dated Nov. 12, 2013 for PCT/IB2012/000907 filed on May 9, 2013 in the name of Probiotical S.P.A.
Del Piano, M. et al. *Evaluation of the intestinal colonization by microencapsulated probiotic bacteria in comparison with the same uncoated strains*. Journal of Clinical Gastroenterology, vol. 44, pp. S42-S46, Sep. 2010.
Cheikhyoussef, A. et al. *Antimicrobial activity and partial characterization of bacteriocin-like inhibitory substances (BLIS) produced by Bifidobacterium infantis BCRC 14602*. Food Control, Butterworth, London, GB, vol. 20 (6), pp. 553-559, Jun. 2009.
Kim, J. et al. *Antimicrobial effect of Bifidobacteriumbreve and Bifidobacteriuminfantis against Salmonella typhimurium KCTC 1925 and E.coli*. Food Science and Biotechnology, Korean Society of Food Science and Technology, vol. 11 (1), pp. 89-92, Jan. 2002.
Candela, M. et al. *Interaction of probiotic Lactobacillus and Bifidobacteriun strains with human intestinal epithelial cells: Adhesion properties, competition against enteropahtogens and modulation of IL-8 production*. International Journal of Food Microbiology, vol. 125 (3), pp. 286-292, Jul. 2008.
PCT International Search Report dated Dec. 16, 2011 for PCT/IB2011/000561 filed on Mar. 17, 2011 in the name of Probiotical S.P.A.
PCT Written Opinion dated Dec. 16, 2011for PCT/IB2011/000561 filed on Mar. 17, 2011 in the name of Probiotical S.P.A.
PCT International Preliminary Report on Patentability dated Sep. 17, 2013 for PCT/IB2011/000561 filed on Mar. 17, 2011 in the name of Probiotical S.P.A.
Peran, L., et al., A comparative study of the preventative effects exerted by three probiotics, Bifidobacterium lactis, Lactobacillus casei and Lactobacillus acidophilus, in the TNBS model of rat colitis, J. Applied Microbiology 2007, 103: 836-844.
Zanoni, S., et al., Growth kinetics on oligo- and polysaccharides and promising features of three antioxidative potential probiotic strains, J. Applied Microbiology 2008, 105: 1266-1276.

Meei-yn, L., et al., Axtioxidative effect of intestinal bacteria Bifidobacterium longum ATCC 15708 and Lactobacillus acidophilus ATCC 4356, Digestive Diseases & Sciences 2000, 45: 1617-1622.
PCT International Search Report dated Mar. 29, 2012 for PCT/IB2012/000095 filed on Jan. 24, 2012 in the name of Probiotical S.p.A.
PCT Written Opinion dated Mar. 29, 2012 for PCT/IB2012/000095 filed on Jan. 24, 2012 in the name of Probiotical S.p.A.
PCT International Preliminary Report on Patentability dated Jul. 30, 2013 for PCT/IB2012/000095 filed on Jan. 24, 2012 in the name of Probiotical S.p.A.
Wikipedia, "Strain (biology)" https://en.wikipedia.org/wiki/Strain_(biology) Retrieved on Nov. 3, 2015. 2 pgs.
"7th Probiotics & Prebiotics—new food", Universita Urbaniana, Rome. Poster 66: "Effectiveness of the Two Microorganisms L. Fermentum LF15 and L. Plantarum LP01, Formulated in Slow Release Vaginal Tablets, in Women Affected by Bacterial Vaginosis (BV): A Pilot Study", Jul. 2013. 52 pages.
"Sachet" Webpage from Merriam-Webster.com, Oct. 7, 2011, accessed via WayBackMachine.com. 1 page.
Alam, M. et al. "Development and Evaluation of Acid-buffering Bioadhesive Vaginal Tablet for Mixed Vaginal Infections" AAPS PharmSciTech 2007; vol. 8, No. 4, Article 109. pp. E1-E8.
Al-Wahsh, I. et al. "Acute probiotic ingestion reduces gastrointestinal oxalate absorption in healthy subjects." Urological Research, vol. 40(3), pp. 191-196. Aug. 2011.
Bordoni, A. et al. "Cholesterol-lowering probiotics: in vitro selection and in vivo testing of bifidobacteria" Applied Microbiology and Biotechnology. Sep. 2013. vol. 97, No. 18 pp. 8273-8281.
Briczinski, E. et al. "Strain-Specific Genotyping of *Bifidobacterium animalis* subsp. Lactis by Using Single-Nucleotide Polymorphisms, Insertions, and Deletions" Applied and Environmental Microbiology. Dec. 2009. vol. 75, No. 23, pp. 7501-7508.
Castro-Leyva, V. et al. "Preserved Ex Vivo Inflammatory Status in Decidual Cells from Women with Preterm Labor and Subclinical Intrauterine Infection." Plos One, vol. 7 (8), e43605, pp. 1-6. Aug. 2012.
Grill et al. "Bile salt toxicity to some bifidobacteria strains: Role of conjugated bile salt hydrolase and pH" Canadian Journal of Microbiology. Oct. 2000, 46, pp. 878-884.
Guo, X. "Basics and Application of Probiotics" Science and Technology Press, 1st Version, Oct. 2002. 2 pages (Chinese Original. English Translation in NPL Reference No. 42).
Hoesl, C. E. et al. "The Probiotic Approach: An Alternative Treatment Option in Urology" European Urology, vol. 47, No. 3, pp. 288-296. Mar. 2005.
http://intranet.comunidadandina.org/Documentos/Gacetas/Gace722.PDF Breach Action Filed by the General Secretary of the Andean Community Against the Republic of Peru, Process 89-AI-2000 (Gaceta Oficial, del Acuerdo de Cartagena, Sumario, Tribunal de Justicia de la Comunidad Andina), Ano XVIII, No. 722, Lima, Oct. 12, 2001, 44 pgs. Spanish with English Abstract.
http://www.ub.es/legmh/capitols/sunyenegre.pdf Dr. Jose Ma Sune Negre, New Galenic Formulations to Forms of Administration (Nuevas Aportaciones Galenicas a las Formas de Administracion. En: Curos de formacion continuada para farmaceuticos de hospital. Fundacion Promocion Medica. Barcelona, 2002, 3, pp. 27-65), 3.2. 27 pgs. Spanish with English Abstract.
Keersmaecker, S. et al. "Strong antimicrobial activity of Lactobacillus rhamnosus GG against *Salmonella typhimurium* is due to accumulation of lactic acid" Federation of European Microbiological Societies Microbiology Letters 259. (2006) 89-96.
Klaver et al. "The Assumed assimilation of cholesterol by lactobacilli and Bifidobacterium bifidum is due to their bile salt-deconjugating activity" Appl Environ Microbiology, 1993, vol. 59, No. 4, pp. 1120-1124.
Lin, M., et al., *Inhibition of lipid peroxidation by Lactobacillus acidophilus and Bifidobacterium longum*, J. Agricultural & Food Chemistry 1999, 47: 3661-3664.
Macfarlane et al., "Review article: prebiotics in the gastrointestinal tract." Aliment. Pharmacol. Ther. 24: 701-714 (2006).

(56) References Cited

OTHER PUBLICATIONS

Mei, X. et al. "Manual of New Drug and Special Drug" Technology Press, 2nd Version, Jan. 2001. 2 pages.
Milani, C. et al., "Comparative Genomics of *Bifidobacterium animalis* subsp. *lactis* Reveals a Strict Monophyletic Bifidobacterial Taxon", Applied and Environmental Microbiology, 79 (14), 2013, 4304-4315.
Mogna, L. et al. "Assessment of the in vitro inhibitory activity of specific probiotic bacteria against different *Escherichia coli* strains." Journal of Clinical Gastroenterology, vol. 46, Supp. 1, pp. S29-S32. Oct. 2012.
Okombo et al., "Probiotic-induced reducetion of gastrointestinal oxalate absorption in healthy subjects." Urol. Res. 201 O: 169-178 (2010).
Pascual, L. et al. "Vaginal Colonization and Activity of the Probiotic Bacterium *Lactobacillus fementum* L23 in a Murine Model of Vaginal Tract Infection", Journal of Medical Microbiology, vol. 59, No. 3, pp. 360-364, Nov. 2009.
Saggioro, A. "Probiotics in the Treatment of Irritable Bowel Syndrome." Journal of Clinical Gastroenterology, vol. 38(6), pp. S104-S106. Jul. 2004.
Strus, M. et al. "Studies on the Effects of Pro Biotic Lactobacillus Mixture Given Orally on Vaginal and Rectal Colonization and on Parameters of Vaginal Health in Women with Intermediate Vaginal Flora" European Journal of Obstetrics Gynecology and Reproductive Biology, vol. 163, No. 2 pp. 210-215. Aug. 2012.
Vicariotto, F. et al: "65: Effectiveness of an Association of a Cranberry Dried Extract, D-Mannose and the Three Microorganisms L. Plantarum Lp01, L. Paracasei, Lpc09 and S. Thermophilus St10 in Women Affected by Cystitis: A Pilot Study", 7th Probiotics & Prebiotics New Foods, pp. 1-52, Jul. 2013.
Wikipedia "Pharmaceutical Drug" Updated Apr. 15, 2016. Downloaded from the internet Apr. 21, 2016. 11 pages.
Kim, H.S. et al. "In vitro Antioxidative Properties of Lactobacilli" Asian-Aust. J. Anim. Sci. 2006; vol. 19; No. 2; pp. 262-265.
Yoon, Y. et al. "Occurrence of Glutathione Sulphydryl (GSH) and Antioxidant Activities in Probiotic *Lactobacillus* spp." Asian-Aust. J. Anim. Sci, 2004; vol. 17; No. 11; pp. 1582-1585.
Liu, J-R. et al. "Antioxidative Activities of Kefir" Asian-Aust. J. Anim. Sci, 2005; vol. 18. No. 4; pp. 567-573.
Van Hemert, Et al. "Influence of the Multispecies Probiotic Ecologic Barrier on Parameters of Intestinal Barrier Function" Food and Nutrition Sciences, 2014, 5, pp. 1739-1745.
Guardamagna et al. "Bifidobacteria supplementation: Effects on plasma lipid profiles in dyslipidemic children" Nutrition, 2014; vol. 30; pp. 831-836.
Shigeru Kamiya, "Igaku no Ayumi" Journal of Clinical and Experimental Medicine, 2003; vol. 207; No. 10, pp. 894-898 (Japanese original + English translation).
Masashi Okamura, "Youkei no Tomo", 2008, vol. 558, pp. 17-21 (Japanese original + English translation).
Yutaka Kanamori, Joumyaku Keichou Eiyou "Parenteral and Enteral Nutrition", 2010, vol. 25; No. 4, pp. 923-928 (Japanese original + English translation).
Federici, et al. "Characterization and Heterologous Expression of the Oxalyl Coenzyme A Decarboxylase Gene from Bifidobacterium lactis" Applied and Environmental Microbiology, Sep. 2004; vol. 70; No. 9; pp. 5066-5073.
Lieske, et al. "Use of a probiotic to decrease enteric hyperoxaluria" Kidney International; 2005; vol. 68; pp. 1244-1249.
Turroni, et al. "Oxalate consumption by lactobacilli: evaluation of oxalyl-CoA decarboxylase and formyl-CoA transferase activity in Lactobacillus acidophilus" Journal of Applied Microbiology; 2007; vol. 103; pp. 1600-1609.
Cremonini et al. "Effect of Different Probiotic Preparations on Anti-Helicobacter pylori Therapy-Related Side Effects: A Parallel Group, Triple Blind, Placebo-Controlled Study" Am. J. Gastroenterol.; 2002; vol. 97; pp. 2744-2749.
Gurbuz, et al. "Effect of N-Acetyl Cysteine on Helicobacter pylori" Southern Medical Journal; Nov. 2005; vol. 98; No. 11; pp. 1095-1097.
Candela, et al. "High taxonomic level fingerprint of the human intestinal microbiota by Ligase Detection Reaction—Universal Array approach" BMC Microbiology; 2010; vol. 10; No. 116; 16 pages.
Chilean First Examination report dated Feb. 12, 2016 for Chilean application No. 2013-002148 filed on Jul. 26, 2013 in the name of Probiotical S.P.A., 21 pgs. Spanish with English translation.
European Patent Office Communication pursuant to Article 94(3) EPC in relation to Application No. 12 780 278.3-1401. dated Jun. 6, 2015 4 pages.
First Office Action for Chinese Patent Application No. 201280015994.3 dated Mar. 25, 2016. 23 pages. (Chinese original + English translation).
Japanese Patent Office Official Action for Japanese Patent Application No. 2013-550962. dated Dec. 1, 2015. 10 pages. (Japanese original + English translation).
Japanese Patent Office Official Action Summary for Japanese Patent Application No. 2014-509850 filed on behalf of Probiotical S.P.A. dated Feb. 16, 2016. (Japanese original + English translation) 5 pages.
Office Action for Russian Patent Application No. 2013137656/15(056766) filed Jan. 24, 2012 on behalf of Probiotical S.P.A. dated Mar. 18, 2016. 10 pages (Russian original + English translation).
Opposition filed to Application No. SP-2013-12844. 14 pages. Spanish original with English Translation; dated Nov. 17, 2015.
Office Action for Russian patent application No. 2014107771/10(012274) filed on behalf of Probiotical S.P.A. dated Jun. 2, 2016. 8 pages (Russian original + English translation).
Final Office Action for U.S. Appl. No. 13/982,255, filed Nov. 12, 2013 on behalf of Giovanni Mogna. dated Sep. 17, 2015. 15 pages.
Notice of Allowance for U.S. Appl. No. 13/982,255, filed Nov. 12, 2013 on behalf of Giovanni Mogna. dated Jan. 22, 2016. 10 pages.
Notice of Allowance for U.S. Appl. No. 13/982,255, filed Nov. 12, 2013 on behalf of Giovanni Mogna. dated Jun. 15, 2016. 11 pages.
Notice of Allowance for U.S. Appl. No. 13/982,255, filed Nov. 12, 2013 on behalf of Giovanni Mogna. dated Jul. 27, 2016. 9 pages.
Non-Final Office Action for U.S. Appl. No. 14/117,003, filed Dec. 27, 2013 on behalf of Giovanni Mogna. dated Oct. 14, 2015. 18 pages.
Final Office Action for U.S. Appl. No. 14/117,003, filed Dec. 27, 2013 on behalf of Giovanni Mogna. dated Jun. 2, 2016. 11 pages.
Non-Final Office Action for U.S. Appl. No. 14/116,996, filed Dec. 18, 2013 on behalf of Giovanni Mogna. dated May 21, 2015. 29 pages.
Final Office Action for U.S. Appl. No. 14/116,996, filed Dec. 18, 2013 on behalf of Giovanni Mogna. dated Mar. 7, 2016. 22 pages.
Restriction Requirement for U.S. Appl. No. 14/344,047, filed Jul. 28, 2014 on behalf of Giovanni Mogna. dated Feb. 19, 2016. 8 pages.
Restriction Requirement for U.S. Appl. No. 14/344,021, filed May 9, 2014 on behalf of Giovanni Mogna. dated Aug. 14, 2015. 7 pages.
Non-Final Office Action for U.S. Appl. No. 14/344,021, filed May 9, 2014 on behalf of Giovanni Mogna. dated Apr. 18, 2016. 29 pages.
Restriction Requirement for U.S. Appl. No. 14/891,306, filed Nov. 13, 2015 on behalf of Giovanni Mogna. dated Apr. 13, 2016. 7 pages.
Office Action Inquiry for Russian Patent Application No. 2013144267 filed Mar. 17, 2011 on behalf of Probiotical S.P.A. dated Mar. 12, 2015 5 pages. English Translation.
Japanese Patent Office Official Action for Japanese Patent Application No. 2013-558517. dated Mar. 3, 2015. 4 pages. (Japanese original + English translation).
First Office Action for Chinese Patent Application No. 201180070870.0 dated Feb. 15, 2016. 15 pages. (Chinese original + English translation).
Japanese Patent Office Official Action for Japanese Patent Application No. 2014-509849. dated Apr. 26, 2016. 9 pages. (Japanese original + English translation).

(56) References Cited

OTHER PUBLICATIONS

Japanese Patent Office Official Action for Japanese Patent Application No. 2014-529081. dated May 31, 2016. 4 pages. (Japanese original + English translation).
Anukam et al., "*Lactobacillus plantarum* and *Lactobacillus fermentum* with Probiotic Potentials Isolated from the Vagina of Healthy Nigerian Women", Research Journal of Microbiology vol. 2 (2007), pp. 81-87.
Decision to Grant a Patent for Invention issued for Russian application No. 2013148474 filed May 9, 2012. dated May 19, 2017. 11 pgs (English Translation and Russian Original).
Del Piano M. et al. "Evaluation of the intestinal colonization by microencapsulated probiotic bacteria in comparison with the same uncoated strains". J Clin Gastroenterol., Sep. 2010; vol. 44, No. Supp. 1, pp. S42-S46.
Final Office Action issued for U.S. Appl. No. 14/344,047, filed Jul. 28, 2014 on behalf of Giovanni Mogna. dated Aug. 4, 2017. 29 pages.
Modesto M. et al. "Resistance to freezing and freeze-drying storage processes of potential probiotic bifidobacteria" Annals of Microbiology, 2004, 54(1), pp. 43-48.
Non-Final Office Action issued for U.S. Appl. No. 15/265,706, filed Sep. 14, 2016 on behalf of Probiotical S.P.A. dated Jul. 11, 2017. 14 pages.
Non-Final Office Action issued for U.S. Appl. No. 14/344,021, filed May 9, 2014 on behalf of Giovanni Mogna. dated Jul. 24, 2017. 18 pages.
Notice of Allowance issued for U.S. Appl. No. 14/117,003, filed Dec. 27, 2013 on behalf of Giovanni Mogna. dated Jul. 6, 2017. 10 pages.
Restriction Requirement issued for U.S. Appl. No. 14/891,321, filed Nov. 13, 2015 on behalf of Probiotical S.P.A. dated Jun. 16, 2017. 6 pages.
"DeNol" 2009; found on the internet Mar. 29, 2016; www.rlsnet.ru/tn_index_id_6426.htm; 6 pages (Russian original + English translation of relevant parts).
Aloisio et al. "Characterization of *Bifidobacterium* spp. Strains for the treatment of enteric disorders in newborns" Appl. Microbiol. Biotechnol., 2012, vol. 96, pp. 1561-1576 + 1 supplemental page.
Antao et al. "The chicken as a natural model for extraintestinal infections caused by avian pathogenic *Escherichia coli* (APEC)" Microbial Pathogenesis, Nov.-Dec. 2008, vol. 45, No. 5-6, pp. 361-369—Abstract Only.
Baluka et al. "PCR-Based Detection of Genes Responsible for Oxalate Detoxification in Probiotic Microorganisms" Eastern Illinois University, Department of Biological Sciences.
Barber et al. "Strengths and Limitations of Model Systems for the Study of Urinary Tract Infections and Related Pathologies" Microbiology and Molecular Biology Reviews, Jun. 2016, vol. 80, No. 2, pp. 351-367.
Bespalov, V.G. et al. "Biologically active food supplements" Kafedra, 2000; pp. 38-47 (Russian original + English translation of relevant parts).
Best et al. "Models for the study of Clostridium difficile infection" Gut Microbes, Mar.-Apr. 2012, vol. 3, No. 2, pp. 145-167.
Broadbent et al. "Biochemistry, Genetics, and Applications of Exopolysaccharide Production in *Streptococcus thermophiles*: A Review" J. Dairy Sci., 2003, 86, pp. 407-423.
Busch et al. "A Model of Infected Burn Wounds Using *Escherichia coli* O18:K1:H7 for the Study of Gram-Negative Bacteremia and Sepsis" Infection and Immunity, Jun. 2000, vol. 68, No. 6, pp. 3349-3351.
Chen et al. "Probiotic Lactobacillus casei Expressing Human Lactoferrin Elevates Antibacterial Activity in the Gastrointestinal Tract" Biometals, 2010, vol. 23, pp. 543-554.
Del Piano, M. et al. "Correlation between chronic treatment with Proton Pump Inhibitors (PPIs) and bacterial overgrowth in the stomach: any possible beneficial role for selected lactobacilli?" J. Clin. Gastroenterol., 48 Suppl 1: S40-6. 13 pgs. Nov.-Dec. 2014.

First Office Action for Chinese Patent Application No. 201280022854.9 dated Nov. 4, 2014 filed on May 9, 2012 in the name of Probiotical S.P.A. (English + Chinese). 15 pages.
Fourth Office Action for Chinese Patent Application No. 201280022854.9 dated Feb. 13, 2017 filed on May 9, 2012 in the name of Probiotical S.P.A. (English + Chinese). 12 pages.
Germond, J.E. et al. "Evolution of the bacterial species Lactobacillus delbrueckii: a partial genomic study with reflections on prokaryotic concept." Mol. Biol. Evol. vol. 20(10, pp. 93-104. Jan. 2003 (Abstract Only).
Guonong et al. China; Light Industry Press, 1st Edition in 2009, Publication Date: Aug. 31, 2009. pp. 363 (Chinese original + English excerpt).
Hamilton-Miller, "The role of probiotics in the treatment and prevention of Helicobacter pylori infection", International Journal of Antimicrobial Agents Oct. 2003 LNKD—PUBMED 14522098, vol. 22, No. 4, Oct. 2003, pp. 360-366, XP002661415.
Karamanolis et al. "A Glass of Water Immediately Increases Gastric pH in Healthy Subjects" Dig. Dis Sci., 2008, vol. 53, pp. 3128-3132.
Khavkin, A.I. et al. "Modern principles of ulcer disease" 2009; found on the internet Mar. 29, 2016; www.lvrach.ru/2005/02/4532114/; 6 pages (Russian original + English translation of relevant parts).
Kizerwetter-Swida et al. "Selection of Potentially Probiotic Lactobacillus Strains Towards their Inhibitory Activity against Poultry Enteropathogenic Bacteria" Polish Journal of Microbiology, 2005, vol. 54, No. 4, pp. 287-294.
Krosnyuk, I.I. et al. "Pharmaceutical technology: Technology of dosage forms: a textbook for university students" Academia editorial center; 2006; p. 6 47 (Russian original + English translation of relevant parts).
Lin, et al., "Antioxidative effect of intestinal bacteria Bifidobacterium longum ATCC 15708 and Lactobacillus acidophilus ATCC 4356", Digestive Diseases & Sciences 2000, 45: 1617-1622.
Moen et al. "Testing the Efficacy and Toxicity of Adenylyl Cyclase Inhibitors against Enteric Pathogens Using in Vitro and in Vivo Models of Infection" Infection and Immunity, Apr. 2010, vol. 78, No. 4, pp. 1740-1749.
Mogna et al. "In Vitro Inhibition of Klebsiella pneumoniae by *Lactobacillus delbrueckii* Subsp. delbrueckii LDD01 (DSM 22106): An Innovative Strategy to Possibly Counteract Such Infections in Humans?" J. Clin. Gastroenterol. Nov.-Dec. 2016, vol. 50, Supp. 2, pp. S136-S139.
Official Action for Russian Patent Application No. 2013151611 filed Apr. 18, 2012 on behalf of Giovanni Mogna. 12 pages (Russian original + English translation).
PCT International Search Report for PCT/IB2012/000779 filed on Apr. 18, 2012 in the name of Giovanni Mogna. dated Jul. 19, 2012.
PCT International Search Report for PCT/IB2014/000731 filed on May 14, 2014 in the name of Probiotical S.P.A. dated Jul. 25, 2014 7 pages.
PCT International Search Report for PCT/IB2014/000739 filed on May 14, 2014 in the name of Probiotical S.P.A. dated Jul. 31, 2014 8 pages.
PCT International Preliminary Report on Patentability for PCT/IB2012/001745 filed on Sep. 10, 2012 in the name of Probiotical North America Inc. dated Mar. 12, 2014 8 pages.
PCT International Preliminary Report on Patentability for PCT/IB2014/000739 filed on May 14, 2014 in the name of Probiotical S.P.A. dated Nov. 26, 2015. 15 pages.
PCT Written Opinion for PCT/IB2012/000779 filed on Apr. 18, 2012 in the name of Giovanni Mogna. dated Jul. 19, 2012.
PCT Written Opinion for PCT/IB2014/000731 filed on May 14, 2014 in the name of Probiotical S.P.A. dated Jul. 25, 2014 10 pages.
PCT Written Opinion for PCT/IB2014/000739 filed on May 14, 2014 in the name of Probiotical S.P.A. dated Jul. 31, 2014 11 pages.
Qingbin et al. Science Press, 1st Edition, Publication Date: Jun. 30, 2012. pp. 118-123 (Chinese original + English excerpt).
Ritchie "Animal Models of Enterohemorrhagic *Escherichia coli* Infection" Microbiology Spectrum, Aug. 15, 2014, 13 pages.
Santini et al. "Characterization of probiotic strains: An application as feed additives in poultry against Campylobacter jejuni" International Journal of Food Microbiology, 2010, vol. 141, pp. S98-S108.

(56) References Cited

OTHER PUBLICATIONS

Second Office Action for Chinese Patent Application No. 201280034204.6 dated Oct. 21, 2016 filed in the name of Probiotical S.P.A. (English + Chinese). 17 pages.
Sgouras Dionyssios N, et al., "Lactobacillus johnsonii La1 attenuates Helicobacter pylori-associated gastritis and reduces levels of proinflammatory chemokines in C57BL/6 mice", Clinical and Diagnostic Laboratory Immunology, American Society for Microbiology, US, vol. 12, No. 12, Dec. 1, 2005, pp. 1378-1386.
Shim et al. "Antimicrobial activity of lactobacillus strains against uropathogens" Pediatrics International, 2016, vol. 58, pp. 1009-1013.
Shu, Q. et al. "Immune protection mediated by the probiotic Lactobacillus rhamnosus HN001 (DR20) against *Escherichia coli* O157:H7 infection in mice" FEMS Immunology and Medical Microbiology. 2002, 34, 59-64.
Terris et al. "Dietary Supplementation with Cranberry Concentrate Tablets May Increase the Risk of Nephrolithiasis" Urology, 2001, 57(1), pp. 26-29.
The EFSA Journal, "Opinion of the Scientific Panel on Additives and Products or Substances used in Animal Feed on the updating of the criteria used in the assessment of bacteria for resistance to antibiotics of human and veterinary importance", 2005, 223, pp. 1-12.
Third Office Action for Chinese Patent Application No. 201280022854.9. dated May 17, 2016. 12 pages. (Chinese original + English translation).
Tsai et al. "Three Lactobacillus strains from healthy infant stool inhibit enterotoxigenic *Escherichia coli* grown in vitro" Anaerobe, Apr. 2008, vol. 14, No. 2, pp. 61-67—Abstract Only.
Vasiljevic et al., "Probiotics-From Metchnikoff to bioactives", International Dairy Journal, Elsevier Applied Science, Barking, GB, vol. 18, No. 7, Jul. 1, 2008, pp. 714-728, XP022701025.
Vicariotto "Effectiveness of an Association of a Cranberry Dry Extract, D-Mannose, and the Two Microorganisms Lactobacillus plantarum LP01 and Lactobacillus paracasei LPC09 in Women Affected by Cystitis" Journal of Clinical Gastroenterology, Nov. 2014, vol. 48, Supp.1, S96-S101.
Wang Kuan-Yuan, et al: "Effects of ingesting Lactobacillus- and Bifidobacterium-containing yogurt in subjects-with colonized Helicobacter pylori", The American Journal of Clinical Nutrition, American Society for Nutrition, US, vol. 80, No. 3, Sep. 1, 2004, pp. 737-741.
Restriction Requirement for U.S. Appl. No. 14/113,211, filed Nov. 26, 2013 on behalf of Giovanni Mogna. dated Sep. 5, 2014. 9 pages.
Non-Final Office Action for U.S. Appl. No. 14/113,211, filed Nov. 26, 2013 on behalf of Giovanni Mogna. dated Apr. 22, 2015. 13 pages.
Non-Final Office Action for U.S. Appl. No. 14/113,211, filed Nov. 26, 2013 on behalf of Giovanni Mogna. dated Jan. 22, 2016. 13 pages.
Final Office Action for U.S. Appl. No. 14/113,211, filed Nov. 26, 2013 on behalf of Giovanni Mogna. dated Nov. 22, 2016. 12 pages.
Notice of Allowance for U.S. Appl. No. 14/117,003, filed Dec. 27, 2013 on behalf of Giovanni Mogna. dated Nov. 9, 2016. 7 pages.
Non-Final Office Action for U.S. Appl. No. 14/344,047, filed Jul. 28, 2013 on behalf of Giovanni Mogna. dated Oct. 13, 2016. 27 pages.
Final Office Action for U.S. Appl. No. 14/344,021, filed May 9, 2014 on behalf of Giovanni Mogna. dated Jan. 31, 2017. 19 pages.
Non-Final Office Action for U.S. Appl. No. 14/891,306, filed Nov. 13, 2015 on behalf of Giovanni Mogna. dated Nov. 22, 2016. 37 pages.
Wiktionary "Cluster—definition" retrieved from the internet on Apr. 27, 2017 from http://web.archive.org/web/20100214060846/https://en.wiktionary.org/wiki/cluster.
Ventura et al. "Identification and Tracing of *Bifidobacterium* Species by Use of Enterobacterial Repetitive Intergenic Consensus Sequences" Applied and Environmental Microbiology, vol. 69, No. 7, Jul. 2003, pp. 4296-4301.

Advisory Action issued for U.S. Appl. No. 14/344,047, filed Jul. 28, 2014 on behalf of Probiotical S.P.A. dated Nov. 28, 2017. 13 pages.
Darouiche, et al. "Bacterial Interference for Prevention of Urinary Tract Infection: A Prospective, Randomized, Placebo-Controlled, Double-Blind Pilot Trial", Clinical Infectious Diseases, vol. 41, Nov. 2005, pp. 1531-1534.
Decision of Rejection for CN201280022854 filed on behalf of Probiotical S.P.A. on Nov. 11, 2013. dated Sep. 8, 2017. Chinese with English translation. 18 pgs.
Final Office Action issued for U.S. Appl. No. 15/265,706, filed Sep. 14, 2016 on behalf of Probiotical S.P.A. dated Feb. 2, 2018. 34 pages.
Final Office Action issued for U.S. Appl. No. 14/116,996, filed Dec. 18, 2013 on behalf of Probiotical S.P.A. dated Dec. 14, 2017. 18 pages.
Final Office Action issued for U.S. Appl. No. 14/346,941, filed Mar. 24, 2014 on behalf of Probiotical S.P.A. dated Jan. 22, 2018. 14 pages.
Final Office Action issued for U.S. Appl. No. 14/891,321, filed Nov. 13, 2015 on behalf of Probiotical S.P.A. dated Apr. 25, 2018. 8 pages.
Final Office Action issued for U.S. Appl. No. 14/891,306, filed Nov. 13, 2015 on behalf of Probiotical S.P.A. dated Jan. 18, 2018. 41 pages.
Giglione, et al. "The Association of *Bifidobacterium breve* BR03 and B632 is Effective to Prevent Colics in Bottle-fed Infants", J Clin Gastroenterol, vol. 50, Supp. 2, Nov. 2016, S164-S167, 4 pgs.
Grimaud, et al. "In vitro screening of probiotic lactic acid bacteria and prebiotic glucooligosaccharides to select effective synbiotics", Anaerobe, vol. 16 (5), Oct. 2010, pp. 493-500. 9 pgs.
Klemenak, et al. "Administration of *Bifidobacterium breve* Decreases the Production of TNF-a in Children with Celiac Disease", Dig Dis Sci, Springer, Jul. 2015, 7 pgs.
Matthews, et al. "Sodium bicarbonate as a single dose antacid in obstetric anaesthesia", Anaesthesia, vol. 44, 1989. pp. 590-591.
McFarland, et al. "Strain-Specificity and Disease-Specificity of Probiotic Efficacy: A Systematic Review and Meta-Analysis", Frontiers in Medicine, vol. 5, Article 124, May 2018, 14 pgs.
Mogna, et al. "Capability of the Two Microorganisms *Bifidobacterium breve* B632 and *Bifidobacterium breve* BR03 to Colonize the Intestinal Microbiota of Children", J Clin Gastroenterol, vol. 48, Supp. 1, Nov. 2014, S37-S39, 3 pgs.
Non-Final Office Action issued for U.S. Appl. No. 14/113,211, filed Nov. 26, 2013 on behalf of Probiotical S.P.A. dated Dec. 7, 2017. 36 pages.
Non-Final Office Action issued for U.S. Appl. No. 14/116,996, filed Dec. 18, 2013 on behalf of Probiotical S.P.A. dated Mar. 27, 2017. 20 pages.
Non-Final Office Action issued for U.S. Appl. No. 14/891,321, filed Nov. 13, 2015 on behalf of Probiotical S.P.A. dated Sep. 6, 2017. 14 pages.
Notice of Allowance issued for U.S. Appl. No. 14/117,003, filed Dec. 27, 2013 on behalf of Probiotical S.P.A. dated Nov. 24, 2017. 5 pages.
Notice of Allowance issued for U.S. Appl. No. 14/344,021, filed May 9, 2014 on behalf of Probiotical S.P.A. dated Dec. 15, 2017. 7 pages.
Notice of Allowance issued for U.S. Appl. No. 14/344,021, filed May 9, 2014 on behalf of Probiotical S.P.A. dated Mar. 27, 2018. 9 pages.
Simone, et al. "The Probiotic Bifidobacterium breve B632 Inhibited the Growth of Enterobacteriaceae within Colicky Infant Microbiota Cultures", Hindawi Publishing Corporation, BioMed Research International, vol. 2014, Aug. 2014, 7 pgs.
Zarate et al. "Protective Effect of Vaginal Lactobacillus paracasei CRL 1289 against Urogenital Infection Produced by *Staphylococcus aureus* in a Mouse Animal Model", Infectious Diseases in Obstetrics and Gynecology, Jan. 2007, 6 pages.
7th Probiotics & Prebiotics New Food, Universita Urbaniana, Rome, Poster 66: "Effectiveness of the Two Microorganisms L. Fermentum LF15 and L. Plantarum LP01, Formulated in Slow Release Vaginal Tablets, in Women Affected by Bacterial Vaginosis (BV): A Pilot Study," Sep. 2013, 52 pages.

(56) References Cited

OTHER PUBLICATIONS

7th Probiotics, Prebiotics & New Foods Proceedings and Abstracts, Retrieved from Internet, [Retrieved on Sep. 2013] URL: Sep. 2013, 206 pages.
Darouiche R.O., et al., "Bacterial Interference for Prevention of Urinary Tract Infection: a Prospective, Randomized, Placebo-controlled, Double-blind Pilot Trial," Clinical Infectious Diseases: An Official Publication of the Infectious Diseases Society of America, Nov. 2005, vol. 41 (10), 4 pages.
Decision to Grant dated May 31, 2017 for Russian Patent Application No. 2013148476/15, filed May 9, 2012 on behalf of Probiotical S.P.A, 15 pages. (Russian Original + 2 pages. Of English Translation).
Decision to Grant dated Sep. 2, 2016 for Russian Patent Application No. 2014110640/05, filed Sep. 21, 2012 on behalf of Probiotical S.P.A., 9 pages.
Douillard F.P., et al., "Comparative Genomic and Functional Analysis of 100 Lactobacillus Rhamnosus Strains and their Comparison with Strain GG," PLOS Genetics, Aug. 2013, vol. 9 (8). 15 pages.
English translations of Non-Patent Literature References 40 and 41: Mei, X., "Manual of New Drug and Special Drug," Technology Press, 2nd Version, Jan. 2001, and Guo, X. "Basics and Application of Probiotics," Oct. 2002, 2 pages.
Final Office Action for U.S. Appl. No. 14/113,211, filed Nov. 26, 2013, on behalf of Hoffmann-Eitle SRL. dated Sep. 28, 2018. 23 pgs.
Final Office Action for U.S. Appl. No. 14/116,996, filed Dec. 18, 2013 on behalf of Giovanni Mogna. dated Dec. 14, 2017. 18 pages.
Final Office Action for U.S. Appl. No. 14/346,941, filed Mar. 24, 2014 on behalf of Probiotical North America Inc. dated Jan. 22, 2018. 14 pages.
Final Office Action for U.S. Appl. No. 14/891,306, filed Nov. 13, 2015 on behalf of Probiotical S.P.A. dated Jan. 18, 2018. 41 pages.
Final Office Action for U.S. Appl. No. 14/891,321, filed Nov. 13, 2015 on behalf of Probiotical S.P.A. dated Apr. 25, 2018. 8 pages.
Final Office Action for U.S. Appl. No. 15/265,706, filed Sep. 14, 2016 on behalf of Probiotical S.P.A. dated Feb. 2, 2018. 34 pages.
First Examination Report dated Mar. 9, 2016 for Chilean application No. 2013002148, filed Jul. 26, 2013, 21 pages.
Fourth Office Action for Chinese Patent Application No. 201280015994.3, filed behalf of Probiotical S.P.A. dated May 22, 2018. 20 pages. (English Translation + Chinese Original).
Gurbuz A.K., et al., "Effect of N-Acetyl Cysteine on Helicobacter Pylori," Southern Medical Journal, Nov. 2005, vol. 98 (11), 4 pages.
Lee, Y.K. et al., "Handbook of Probiotics and Prebiotics", Second Edition (2009), John . Wiley & Sons, Inc. pp. 4, 5 and 24. 5 pages Of English copy.
Mathews H.M., et al., "Sodium Bicarbonate as a Single Dose Antacid in Obstetric Anaesthesia," Anaesthesia, Jul. 1989, vol. 44 (7), 2 pages.
Mogna, L., et al., "Screening of Different Probiotic Strains for Their in Vitro Ability to Metabolise Oxalates: Any Prospective Use in Humans?" Journal of Clinical Gastroenterology, 2014, vol. 48, S91-S95). 5 pages.
Non-Final Office Action for U.S. Appl. No. 13/982,255, filed Nov. 12, 2013 on behalf of Giovanni Mogna. dated Mar. 10, 2015, 19 pages.
Non-Final Office Action for U.S. Appl. No. 14/113,211, filed Nov. 26, 2013 on behalf of Giovanni Mogna. dated Dec. 7, 2017. 36 pages.
Non-Final Office Action for U.S. Appl. No. 14/116,996, filed Dec. 18, 2013 on behalf of Giovanni Mogna. dated Mar. 27, 2017, 20 pages.
Non-Final Office Action for U.S. Appl. No. 14/346,941, filed Mar. 24, 2014 on behalf of Probiotical North America Inc. dated Apr. 19, 2017, 14 pages.
Non-Final Office Action for U.S. Appl. No. 14/891,321, filed Nov. 13, 2015 on behalf of Probiotical S.P.A. dated Sep. 6, 2017, 14 pages.
Notice of Allowance for U.S. Appl. No. 14/117,003, filed Dec. 27, 2013 on behalf of Giovanni Mogna. dated Nov. 22, 2016, 8 pages.
Notice of Allowance for U.S. Appl. No. 14/117,003, filed Dec. 27, 2013 on behalf of Giovanni Mogna. dated Nov. 24, 2017, 5 pages.
Notice of Allowance for U.S. Appl. No. 14/344,021, filed May 9, 2014 on behalf of Giovanni Mogna. dated Dec. 15, 2017. 7 pages.
Notice of Allowance for U.S. Appl. No. 14/344,021, filed May 9, 2014 on behalf of Giovanni Mogna. dated Mar. 27, 2018. 9 pages.
Notice of Allowance for U.S. Appl. No. 14/346,941, filed Mar. 24, 2014 on behalf of Giovanni Mogna. dated Aug. 6, 2018. 8 pages.
Notification of Reexamination for Japanese Patent Application No. JP2014509850 in the name of Probiotical S.P.A, dated Feb. 16, 2016, 5 pages. (Japanese + English).
Office Action for Japanese Patent Application No. JP2016513455, dated Jan. 16, 2018, 7 pages (English Translation+ Japanese Original).
Opposition to Ecuadorian Patent Application SP201313082 on behalf of ALAFAR, 2015, 14 pages (Spanish original + English translation).
Restriction Requirement for U.S. Appl. No. 14/346,941, filed Mar. 24, 2014 on behalf of Probiotical North America Inc. dated Nov. 16, 2016, 8 pages.
Rowe, R.C. et al., "Handbook of Pharmaceutical Excipients", Chemical Industry Press, 4th Edition, pp. 692-693, (Jan. 31, 2005), 9 pages. (English Translation + Chinese Original).
Santini C., et al., "Characterization of Probiotic Strains: an Application as Feed Additives in Poultry Against *Campylobacter Jejuni*," International Journal of Food Microbiology, Jul. 2010, vol. 141 (Suppl 1), pp. S98-S108.
Schillinger U., et al., "Antibacterial Activity of *Lactobacillus sake* Isolated from Meat", Applied and Environmental Microbiology, Aug. 1989, pp. 1901-1906.
Wikipedia "Colony-Forming Unit", Downloaded from the internet Apr. 13, 2017. http://en.wikipedia.org/wiki/Colony-forming unit, 1 page.
Wiktionary "Bifidogenic" Last modified Jul. 19, 2014, Retrieved from the internet on Apr. 13, 2017, from http://en.wiktionary.org/wiki/bifidogenic, 1 page.
Ying D.Y., et al., "Microencapsulated Lactobacillus Rhamnosus Gg Powders: Relationship of Powder Physical Properties to Probiotic Survival During Storage," Journal of Food Science, Nov. 2010, vol. 75 (9), p. E88-E95.
Zarate et al., "Protective Effect of Vaginal *Lactobacillus Paracasei* CRL 1289 Against Urogenital Infection Produced by *Staphylococcus Aureus* in a Mouse Animal Model," Infectious Diseases in Obstetrics and Gynecology, Mar. 2007, 6 pages.
Notification of Reexamination for Chinese Patent Application No. CN201280022854 in the name of Probiotical S.P.A, dated Sep. 29, 2018, 14 pages (Chinese + English).

* cited by examiner

PROBIOTIC BACTERIAL STRAINS AND SYMBIOTIC COMPOSITION CONTAINING THE SAME INTENDED FOR INFANT FOOD

CROSS REFERENCE TO RELATED APPLICATIONS

The present application is the US national stage of International Patent Application PCT/IB2012/000897 filed on May 9, 2012 which, in turn, claims priority to Italian Patent Application MI2011A000793 filed on May 9, 2011.

The present invention relates to a selection of probiotic strains belonging to the genus *Bifidobacterium* and to a symbiotic composition containing the same and intended for infant food.

Infants fed an artificial diet show considerable differences in the composition of intestinal microbiota compared to breastfed infants: in particular, a reduction can be observed in the concentration of bifidobacteria at the expense of other potentially pathogenic microorganisms, such as *Escherichia coli* and *Clostridium* spp. The colonization of microorganisms belonging to the genus *Bifidobacterium* takes place in breastfed infants in the first 4 days after birth and bifidobacteria very soon become the prevalent microbial group. With formula feeding, on the other hand, a more heterogeneous flora composed of coliforms, bacteroides, clostridia and streptococci develops. Precisely for these reasons, formula fed infants have a higher risk of contracting intestinal infections.

In addition, an excessive production of intestinal gas seems to be the cause of so-called "colic", which afflicts numerous infants in the first months of life.

Therefore, there is a felt need to be able to obtain, in infants, the physiologically bifidogenic effect obtained through feeding with breast milk. In particular, it is desirable to be able to guarantee formula fed infants an intestinal flora such as to avoid colic.

The Applicant has provided an answer to the above-mentioned needs following an intense activity of research, at the end of which it identified a selection of bacterial strains belonging to the genus *Bifidobacterium*.

The subject matter of the present invention relates to a bacterial strain belonging to the genus *Bifidobacterium* and having the characteristics as disclosed in the appended independent claim.

The subject matter of the present invention also relates to a food composition or supplement product or pharmaceutical composition containing said bacterial strains, as disclosed in the appended independent claim. Said compositions have valid application for use in the treatment of the colic, diarrhoea and intestinal disorders, preferably in subjects in paediatric age.

Preferred embodiments of the present invention will be illustrated in the detailed description that follows.

Figure 1:
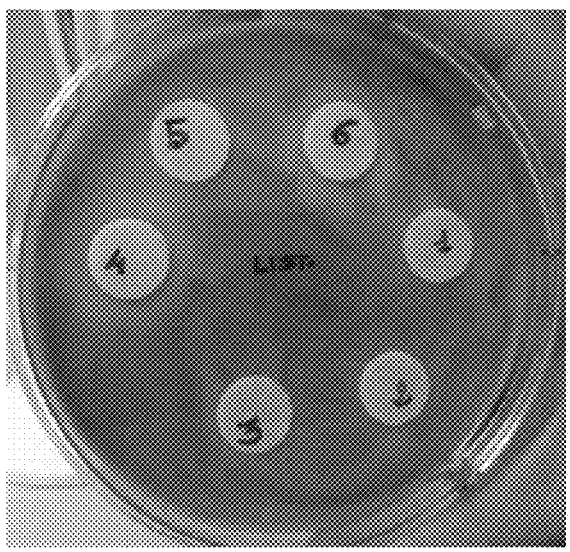
FIG. 1 reports the results of inhibition haloes expressed in millimeters of the following six probiotic strains against *Listeria monocytogenes* ATCC 19112:
1. *L. reuteri* DLLRE08, DSM 25684 0mm
2. *I. reuteri* ID 1774 LRE 02, DSM 23878 0mm
3. *L. reuteri* DSM 17938 (Positive ref.) 0mm
4. *L. plantarum* LP01 LMG P-21021 5mm
5. *L. delbr.* susp. *bulgaricus* LDD01 2mm
6. *L. pentosus* PCB 101 4mm FIG. 2 reports the results of inhibition haloes expressed in millimetres of the following six probiotic strains against *Enterococcus* sp. (from infant faeces). The results are, starting from the arrow in a clockwise direction in the left panel and in a counter-clockwise direction in the right panel:
1. *L. reuteri* DLLRE08, DSM 25684 3mm
2. *L. reuteri* ID 1774 LRE 02, DSM 23878 3mm
3. *L. reuteri* DSM 17938 (Positive ref.) 3mm
4. *L. plantarum* LP01 LMG P-21021 5mm
5. *L. delbr.* susp. *bulgaricus* LDD01 4mm
6. *L. pentosus* PCB 101 2mm The left panel represents a back of plate view and the tight panel represents an inside plate view. The arrow points to No. 1 in both the back of plate view and inside plate view.

The bacterial strains selected by the Applicant have probiotic characteristics and can be administered to infants, as they comply with specific guidelines (FAO/WHO, 2002) which require: an evaluation of the antimicrobial activity toward antagonist bacteria, the non-toxicity and non-pathogenicity of the strain, an accurate taxonomic identification thereof, adhesion to the intestinal epithelium, resistance to the gastrointestinal tract (gastric juice and bile), genetic stability, with particular reference to the transmissibility of antibiotic resistance, and desirable sensory and technological properties when used in an industrial process. Also of particular importance is the study of the cytotoxicity of the probiotics against human cells and verification of their ability to adhere to the intestinal mucosa and ability to block the adhesion of the pathogens to the intestinal cells themselves.

The Applicant selected the strains of the present invention only after having experimentally verified the above-mentioned specifications.

The bacterial strains selected by the Applicant belong to the genus *Bifidobacterium* and have an antimicrobial activity against *E. coli*. Moreover, said strains additionally have an antimicrobial activity against *Salmonella enteriditis*, *Clostridium difficile* and *Campylobacter jejunii*.

The selected strains belong to the species *Bifidobacterium breve* and *Bifidobacterium longum* or *Bifidobacterium longum* subsp. *longum*.

The strains selected by the Applicant are:
(i) *Bifidobacterium breve* B632, deposited by the company Probiotical SpA of Novara (Italy) with the Depositary Institution DSMZ on Apr. 7, 2011 and having the deposit number DSM 24706.
(ii) *Bifidobacterium breve* B2274, deposited by the company Probiotical SpA of Novara (Italy) with the Depositary Institution DSMZ on Apr. 7, 2011 and having the deposit number DSM 24707.
(iii) *Bifidobacterium breve* B7840, deposited by the company Probiotical SpA of Novara (Italy) with the Depositary Institution DSMZ on Apr. 7, 2011 and having the deposit number DSM 24708.
(iv) *Bifidobacterium longum* subsp. *longum* B1975, deposited by the company Probiotical SpA of Novara (Italy) with the Depositary Institution DSMZ on Apr. 7, 2011 and having the deposit number DSM 24709.

All the above strains are available and accessible to the public under the conditions established by the Budapest Treaty.

The food composition or supplement product or pharmaceutical composition of the present invention comprises a bacterial mixture which in turn comprises at least one above-mentioned bacterial strain, for use in the treatment of colic, diarrhoea and intestinal disorders, preferably in subjects in paediatric age.

In one embodiment, the bacterial mixture comprises or, alternatively, consists of strain (i) or (ii) or (iii) or (iv).

In one embodiment, the bacterial mixture comprises or, alternatively, consists of strains (i) and (ii).

In one embodiment, the bacterial mixture comprises or, alternatively, consists of strains (i) and (iii).

In one embodiment, the bacterial mixture comprises or, alternatively, consists of strains (i) and (iv).

In one embodiment, the bacterial mixture comprises or, alternatively, consists of strains (ii) and (iii).

In one embodiment, the bacterial mixture comprises or, alternatively, consists of strains (ii) and (iv).

In one embodiment, the bacterial mixture comprises or, alternatively, consists of strains (iii) and (iv).

In one embodiment, the bacterial mixture comprises or, alternatively, consists of strains (i) and (ii) and (iii).

In one embodiment, the bacterial mixture comprises or, alternatively, consists of strains (i) and (ii) and (iv).

In one embodiment, the bacterial mixture comprises or, alternatively, consists of strains (ii) and (iii) and (iv).

In one embodiment, the bacterial mixture comprises or, alternatively, consists of strains (i) and (iii) and (iv).

In one embodiment, the bacterial mixture comprises or, alternatively, consists of strains (i) and (ii) and (iii) and (iv).

Moreover, the subject matter of the present invention relates to a symbiotic composition comprising at least one of the above-mentioned probiotic bacterial strains in association with at least one prebiotic fibre. Said association advantageously enables a selective multiplication of the existing beneficial bacteria to be obtained, thus inducing advantageous local and systemic effects for the host. The symbiotic composition is intended for infants.

In particular, several "non-digestible oligosaccharides" selected from the group comprising galacto-oligosaccharides (GOS), fructo-oligosaccharides (FOS) and inulin have valid application as fibres in the context of the present invention.

A preferred embodiment relates to a composition comprising a formula for feeding infants, at least one bacterial strain of the present invention and at least one prebiotic fibre selected from among those mentioned above. Advantageously, said composition is capable of providing the infant a marked "bifidogenic" effect very similar to that of human milk.

The subject matter of the present invention relates to a bacterial strain belonging to the species *Bifidobacterium breve*, *Bifidobacterium longum* or *Bifidobacterium longum* subsp. *longum* and having an antimicrobial activity against the pathogens *E. coli*, *Salmonella enteriditis*, *Clostridium difficile* and *Campylobacter jejunii*. The pathogen *E. coli* comprises the biotype *E. coli* O157:H7.

The strain that belongs to the species *Bifidobacterium breve* is selected from the group comprising or, alternatively, consisting of *Bifidobacterium breve* B632, deposited by the company Probiotical SpA of Novara (Italy) with the Depositary Institution DSMZ on Apr. 7, 2011 and having the deposit number DSM 24706; *Bifidobacterium breve* B2274, deposited by the company Probiotical SpA of Novara (Italy) with the Depositary Institution DSMZ on Apr. 7, 2011 and having the deposit number DSM 24707; *Bifidobacterium breve* B7840, deposited by the company Probiotical SpA of Novara (Italy) with the Depositary Institution DSMZ on Apr. 7, 2011 and having the deposit number DSM 24708 and *Bifidobacterium breve* BR03, deposited by the company Probiotical SpA of Novara (Italy) with the Depositary Institution DSMZ and having the deposit number DSM 16604; preferably the strain is *Bifidobacterium breve* BR03, deposited by the company Probiotical SpA of Novara (Italy) with the Depositary Institution DSMZ and having the deposit number DSM 16604. The strain that belongs to the species *Bifidobacterium longum* is *Bifidobacterium longum* subsp. *longum* B1975, deposited by the company Probiotical SpA of Novara (Italy) with the Depositary Institution DSMZ on Apr. 7, 2011 and having the deposit number DSM 24709.

The subject matter of the present invention relates to the strain *Bifidobacterium breve* B632, deposited by the company Probiotical SpA of Novara (Italy) with the Depositary Institution DSMZ on Apr. 7, 2011 and having the deposit number DSM 24706, in association with *Bifidobacterium breve* BR03, deposited by the company Probiotical SpA of Novara (Italy) with the Depositary Institution DSMZ and having the deposit number DSM 16604.

The subject matter of the present invention relates to the strain *Bifidobacterium breve* BR03, deposited by the company Probiotical SpA of Novara (Italy) with the Depositary Institution DSMZ and having the deposit number DSM 16604, in association with *Lactobacillus plantarum* LP01 deposited by the company Mofin Srl of Novara (Italy) with the Depositary Institution BCCM-LMG on Oct. 10, 2001 and having the deposit number LMG P-21021. Advantageously, the strain *Lactobacillus plantarum* LP01 shows a great activity of inhibition against pathogenic strains, as demonstrated in the experimental part that follows (FIGS. 1-5).

The present invention relates to a food composition or supplement product or medical device or pharmaceutical composition comprising a bacterial mixture, said bacterial mixture comprises or, alternatively, consists of at least one bacterial strain belonging to the species *Bifidobacterium breve*, *Bifidobacterium longum* or *Bifidobacterium longum* subsp. *longum*, as described above, for use in the treatment of colic, diarrhoea and intestinal disorders; preferably in subjects in paediatric age. Said bacterial mixture comprises or, alternatively, consists of the strains *Bifidobacterium breve* B632 in association with *Bifidobacterium breve* BR03 or, alternatively, *Bifidobacterium breve* BR03 in association with *Lactobacillus plantarum* LP01. Said food composition or supplement product or medical device or pharmaceutical composition comprises a bacterial mixture, as described above, wherein said bacterial mixture is added or suspended or dispersed in a vegetable oil selected from among olive oil, corn oil, sunflower oil, seed oil and palm oil. Preferably it is a corn oil.

The food composition or supplement product or medical device or pharmaceutical composition can be in the form of an oily suspension or granules, powder, capsules, tablets and sachets.

The subject matter of the present invention relates to a food composition or supplement product or medical device or pharmaceutical composition as a symbiotic composition. Said symbiotic composition comprises at least one vegetable substance selected from the group comprising or, alternatively, consisting of sterols or phytosterols, stanols or phytostanols, glucomannan, konjac gum and/or at least one prebiotic fibre selected from the group comprising fructo-oligosaccharides -FOS, galacto-oligosaccharides -GOS, xylo-oligosaccharides -XOS, inulin, larch fibre or arabinogalactan and/or fermented red rice and/or betaglucans from oats, oat bran, barley, barley bran and/or aloe arborescens gel in lyophilized form. In one embodiment, said symbiotic composition comprises simethicone. In another embodiment, said symbiotic composition comprises at least one vegetable substance selected from the group comprising galacto-oligosaccharides (GOS), fructo-oligosaccharides (FOS) and inulin.

EXPERIMENTAL PART

1. Selection of the *Bifidobacteria*

Forty-six strains of *Bifidobacterium* spp. were studied; they were prevalently isolated from infant faeces and belong to 5 different species (*B. bifidum*, *B. breve*, *B. longum* subsp. *infantis*, *B. longum* subsp. *longum*, *B. adolescentis* and *B. pseudocatenulatum*). The microorganisms considered are part of the BUSCoB collection (Bologna University Scardovi Collection of Bifidobacteria, University of Bologna, Italy) present at the DiSTA.

2. Selection of the Target Pathogenic Microorganisms

Various strains of *Escherichia coli* were taken into consideration: 1 strain of *E. coli* from a collection (ATCC 11105), 1 strain of *E. coli* isolated from faeces during a urinary tract infection (strain M85), which had demonstrated to be a good target microorganism in previous studies, and two strains of *E. coli* isolated from infants affected by colic (strain GC6a and GC23a). *E. coli* is a major etiological agent of acute diarrhoea in children. Furthermore, an examination was made of a strain of *Salmonella enteriditis*, the main microorganism responsible for diarrhoeas of bacterial origin in children in Italy (Infante Pina et al., 2008); a strain of *Clostridium difficile*, a major etiological agent of acute diarrhoea in children (Infante Pina et al., 2008); and a strain of *Campylobacter jejuni*, which is likewise a cause of acute diarrhoea in children (Infante Pina et al., 2008).

3. Study of the Antimicrobial Activity of the Selected Microorganisms

All 46 microorganisms were analyzed for their ability to inhibit the growth of *E. coli* ATCC 11105TM, M85, GC 6a, GC 23a and *S. enteriditis* M94. A preliminary screening for antimicrobial activity was performed using the "spot agar test", according to the protocol briefly summarized here.

SPOT AGAR TEST: use is made of an overnight (o.n.) culture of each strain of *Bifidobacterium*, having an absorbance at 600 nm ($A_{600}$) of about 0.7-1, corresponding to a full exponential phase. A TPY-agar plate is used; the plate is divided into 4 and each quadrant is inoculated with 10 ηl of the o.n. culture of each strain. The plate is incubated 24 h at 37° C. under anaerobiosis. Once growth has occurred, the surface is covered with a 7-8 ml layer of soft agar medium for *E. coli* (NB+0.7% agar), inoculated with 100 ηl of an o.n. culture of the marker strain. The plate is incubated under conditions allowing the growth of the marker strain. After 24-48 hours of incubation, depending on the marker strain used, the presence of an inhibition halo can be observed around the inoculum of each strain of *Bifidobacterium*. This halo is measured with a ruler. The test is repeated at least twice. The results obtained—the average of two experiments—are shown in Table 1. Table 1 shows the inhibition halos produced by the 5 marker strains for only 16 of the 46 strains tested.

TABLE 1

| Strain | *E. coli* ATTC 11105 | *E. coli* M85 | *E. coli* GC 6a | *E. coli* GC 23a | *S. enteriditis* M94 |
| --- | --- | --- | --- | --- | --- |
| B 2274 | 0.8 | 0.8 | 1 | 1 | 1.3 |
| B 632 | 1.2 | 1.2 | 0.8 | 0.9 | 1.2 |
| B 1975 | 0.9 | 0.7 | 0.7 | 0.6 | 1.2 |
| B7840 | 0.7 | 0.7 | 1 | 0.6 | 1 |
| B 2091 | 0.4 | 0.3 | 0.6 | 0.6 | 0.7 |
| B 2021 | 0.6 | 0.6 | 0.9 | 0.9 | 1 |
| B 2150 | 0.6 | 0.6 | 1 | 0.8 | 1 |
| B 2195 | 0.5 | 0.7 | 0.9 | 0.7 | 1.1 |
| Re 12 | 0.9 | 0.6 | 0.8 | 0.8 | 1 |
| B2101 | 0.9 | 1 | 0.9 | 1 | 1 |
| B 8452 | 0.5 | 0.6 | 0.1 | 0.4 | 0.2 |
| B 2192 | 0.9 | 0.7 | 1 | 0.7 | 1.5 |
| B 2055 | 0.7 | 0.9 | 0.3 | 0.5 | 0.5 |
| B 7958 | 0.7 | 0.7 | 0.6 | 0.8 | 1.1 |
| B 7947 | 0.7 | 0.7 | 0.4 | 0.3 | 0.5 |
| B1412 | 1.2 | 1.2 | 1.3 | 0.9 | 1 |

As can be noted from an examination of Table 1, this study revealed the presence of strains with a good antagonistic activity above all against the two strains of *E. coli* isolated from infants with colic and *Salmonella enteriditis*. Only the strains which globally exhibited inhibition haloes of larger size were selected.

The antagonistic activity of the 16 selected strains against *Clostridium difficile* M216 and *Campylobacter jejuni* LMG8841 was then assessed. The results obtained—the average of two experiments—are presented in Table 2.

TABLE 2

Size of the inhibition haloes (in cm) produced by
Clostridium difficile M216 and Campylobacter jejuni LMG8841 for the
16 selected Bifidobacterium strains.

| Strain | C. jejuni LMG8841 | C. difficile M216 |
|---|---|---|
| B2091 | 0.8 | 0.4 |
| B2274 | 1 | 0.5 |
| B2021 | 1 | 0.4 |
| B 632 | 0.8 | 0.5 |
| B2150 | 0.8 | 0.4 |
| B2195 | 1.2 | 0.5 |
| B1412 | 1.1 | 0.5 |
| Re 12 | 1.1 | 0.4 |
| B2101 | 0.8 | 0 |
| B1975 | 0.8 | 0.5 |
| B8452 | 0.8 | 0.4 |
| B2192 | 1 | 0.4 |
| B2055 | 1 | 0.3 |
| B7958 | 1.1 | 0.4 |
| B7947 | 0.3 | 0.3 |
| B7840 | 1.4 | 0.3 |

The results obtained revealed a high inhibitory activity toward *C. jejuni* LMG8846 and a weaker—though distinctly present in the majority of the strains—activity against *C. difficile* M216.

An assessment was then made of the antimicrobial power of the supernatant obtained from o.n. cultures of the 16 selected microorganisms toward two strains isolated from infants affected by colic and toward *S. enteriditis*. The supernatant, having a pH comprised in the interval 5.5-6.2, was brought to pH 6.5 before the test was performed. The assay was performed using two methods briefly described here: "well diffusion assay" and "blank disk test".

Well Diffusion Assay: use is made of an overnight (o.n.) culture of each strain of *Bifidobacterium*, having an $A_{600}$ of about 0.7-1, corresponding to a full exponential phase. The culture is centrifuged at 10000 rpm for 10 minutes; the supernatant is re-centrifuged at 14000 rpm for 15 minutes and immediately re-centrifuged. It is then brought to pH 6.5 with NaOH 1N. A layer of soft agar inoculated with 500 ηL of a suspension of *E. coli* $10^6$ CFU/ml (or of any other marker strain used) is applied on a plate. After the agar has solidified, wells are prepared with a sterile Pasteur pipette and 50-80 ηl of neutralized supernatant of *Bifidobacterium* spp. is introduced into the wells. The plate is incubated o.n. at 37° C. under conditions allowing the growth of the marker strain (37° C. under aerobiosis for *E. coli*).

Blank Disk Method: Centrifugation of the *Bifidobacterium* culture and neutralization of the supernatant were carried out as above. Use is made of a Nutrient Agar (NA) plate in the case of *E. coli* or other media if different strains are used. The marker strain is inoculated onto the surface starting from a suspension having a cellular concentration of $10^6$ CFU/ml. A disk (previously sterilized) having a diameter of one cm is soaked with 0.1 ml of supernatant (both neutralized and non-neutralized) and is rested upon the plate. The plate is incubated under conditions suitable for the growth of the marker strain.

The inhibitory effect of the microorganisms on the marker microorganisms as revealed by the spot agar test seems to be due mainly, but not only, to the production of acidic metabolites which, by lowering the pH of the surrounding environment, bring about an inhibition of the pathogens. However, the production of bacteriocins seems possible.

Nevertheless, in order to better characterize the antimicrobial activity of the supernatant of the microorganisms used in this study, an assessment was made of the growth kinetics of some marker strains (*E. coli* ATCC11105™, *S. enteriditis* M94, *E. coli* GC 6a and *E. coli* GC 23a) in the presence of known amounts of the supernatant of each strain of *Bifidobacterium*. The marker strain was inoculated into the NB (Nutrient Broth) medium with no addition (this represents the control) and in the presence of known amounts of supernatant derived from an o.n. culture of *Bifidobacterium* spp. The supernatant was used both as such and after neutralization at three different concentrations: 12.5% (v/v), 25% (v/v) and 50% (v/v). At defined intervals of time a measurement was made of the $A_{620}$ of the marker strain, indicative of the microorganism's growth. The highest concentration of supernatant was eliminated after the first attempts, because it completely impeded the growth of the marker microorganism.

The data obtained confirm the conclusions set forth above.

4. Determination of the Sensitivity or Resistance of the Selected Bifidobacteria to Different Antibiotics and Determination of the Minimal Inhibitory Concentration (MIC)

Antibiotic sensitivity or resistance testing is one of the basic studies for evaluating the possibility of using a microorganism in in vivo tests. It is important for the microorganism to be as sensitive as possible to the main antibiotics used in therapy in order to avoid the risk of transmitting antibiotic resistance to other intestinal microorganisms; on the other hand, probiotics are often jointly administered with an antibiotic therapy and hence antibiotic resistance becomes a fundamental requisite for co-administration (Ouba et al, 2008). In this study, 10 antibiotics traditionally used to evaluate antibiotic resistance in probiotic strains (ampicillin, chloramphenicol, erythromycin, tetracycline, vancomycin, kanamycin, streptomycin, trimethoprim, cefuroxime and gentamycin) were taken into consideration; they were tested in a concentration interval of 2-1024 μg/ml. Furthermore, the MIC of another three antibiotics commonly used in neonatal therapy (amoxicillin, ceftriaxone and clarithromycin), tested at the same concentrations, was determined. The MIC was evaluated by analyzing the growth of the selected Bifidobacteria in the presence of increasing antibiotic concentrations; growth was evaluated by measuring the $A_{620}$. The resistance or sensitivity to antibiotics was evaluated using the guidelines published by the European Commission (EU commission, 2002) and the European Food Safety Authority (EFSA, 2005).

The results obtained indicate that the selected strains show resistance to ampicillin, kanamycin and amoxicillin, whereas, in general, many of the tested strains showed to be sensitive to the other antibiotics taken in consideration.

The results obtained enabled the selection of the 4 strains of *Bifidobacterium* spp., to which the present invention relates, since they exhibit antimicrobial activity against different strains of *E. coli* (gas-producing bacteria present in higher concentrations in infants that suffer from colic than in infants that do not). Moreover, said strains show an interesting antimicrobial activity against bacteria that are most frequently the cause of diarrhoea of bacterial origin in infants (*Salmonella enteriditis, Clostridium difficile* and *Campylobacter jejunii*) as well as resistance to only a limited number of antibiotics. None of the 4 selected strains demonstrated to be capable of transferring the genes for antibiotic resistance to Bifidibacteria or Lactobacilli, even in the cases where the genes were identified via PCR in the chromosomal DNA of the Bifidobacteria.

5. Method for Testing Inhibition on Plates
Bacteria with Inhibiting Action
   a. The bacterium whose inhibitory activity against faecal bacteria it is intended to verify of undergoes at least two sequential transplants in MRS broth medium (test tubes containing 15 ml).
      i. If the bacterium belongs to the genus *Bifidobacterium*, the MRS broth will be supplemented with 1% Cysteine Chlorohydrate (5% sol.).
   b. The fresh broth culture (cultured 22+/−2 hours) is centrifuged and the cells are washed once in sterile water.
   c. The cells are then centrifuged and resuspended in 5 ml of fresh MRS broth medium.
2. Sensitive faecal bacterium
   a. The bacterium to be subjected to inhibition undergoes at least two sequential transplants in MacConkey broth medium (test tubes containing 10 ml).
   b. The fresh broth culture is diluted in water so as to obtain an optical density of 0.600-0.700 at a wavelength of 600 nm.
   c. 100 ml of this bacterial suspension is applied on a MacConkey agar plate and evenly distributed over the entire surface using a suitable sterile spatula until the liquid has been completely absorbed.
3. An 11 mm diameter paper disk (antibiogram disk) is placed on the surface of the plate, which is made to absorb 100 ml of the bacterial suspension of the strain to be tested (see step 1-c).
4. The plate is incubated in a thermostat at 37° C. for 24 hours.
Results: if the bacterium is inhibiting, a halo indicating no growth will be visible around the disk. The dimensions of the halo will be proportionate to the capability of the strain to produce substances with a bacteriostatic/bactericidal action that spread through the agar.
6. Inhibition Tests on Plates For each potentially inhibiting probiotic, a culture is prepared and incubated for 24 hours in MRS broth. The cells are then washed and resuspended in fresh MRS broth medium. A fresh broth culture of the pathogenic bacterium is evenly spread on the surface of plates containing the agarized medium, specific for the pathogenic species it is intended to inhibit, in an amount of 100 l per plate of the first decimal dilution. The cells thus treated are adsorbed onto a paper disk, in an amount of 100 l per disk. After incubation at 37° C. for 24 hours a measurement is made of the inhibition halo, represented by the area extending between the edge of the disk and the edge of growth of the tested pathogen.

The tests of the inhibition activity of the six probiotics against the five pathogens are listed and represented below. The results are reported as inhibition haloes expressed in millimetres.

Figure 2:
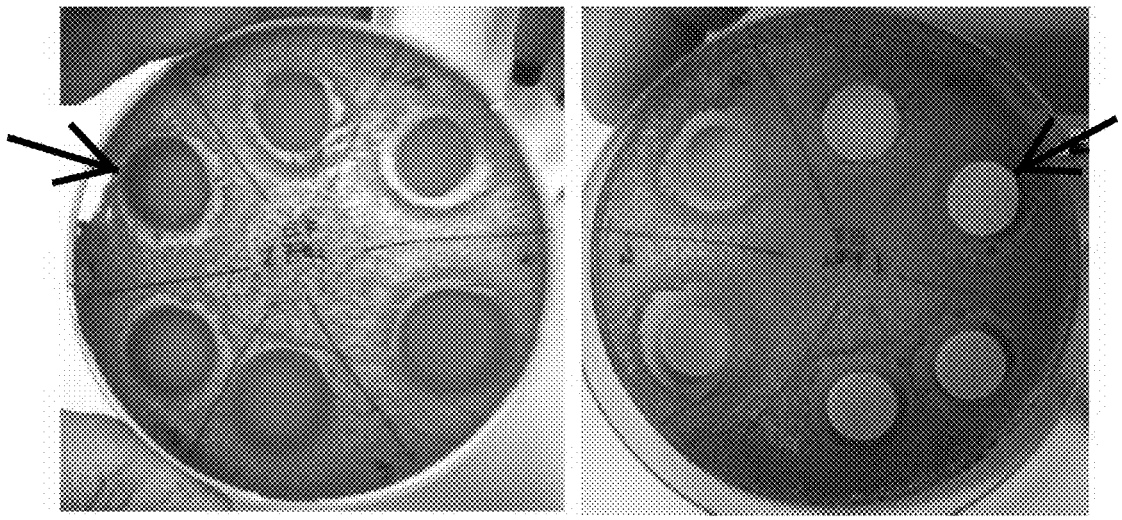
Figure 3:
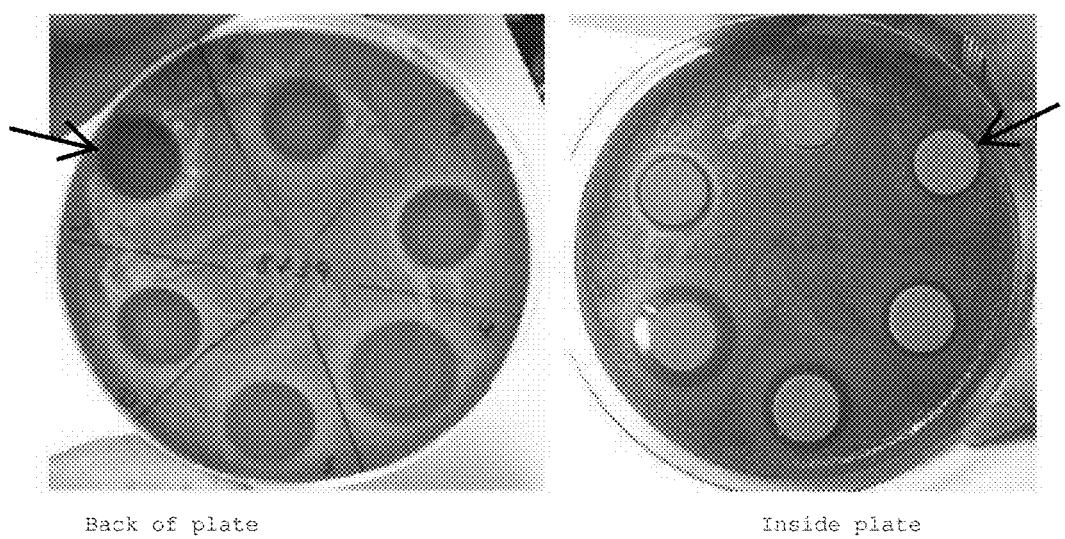
FIG. 3 reports the results of inhibition haloes expressed in millimetres of the following six probiotic strains against *Escherichia coli* ATCC 8739. The results are, starting from the arrow in a clockwise direction in the left panel and in a counter-clockwise direction in the right panel:
1. *L. reuteri* DLLRE08, DSH 25684 0mm
2. *L. reuteri* ID 1774 LRE 02, DSM 23878 1mm
3. *L. reuteri* DSM 17938 (Positive ref.) 2mm
4. *L. plantarum* LP01 LMG P-21021 4mm
5. *L. delbr.* susp. *bulgaricus* LDD01 2mm
6. *L. pentosus* PCB 101 1mm The left panel represents a back of plate view and the right panel represents an inside plate view. The arrow points to No. 1 in both the back of plate view and inside plate view.
Figure 4:
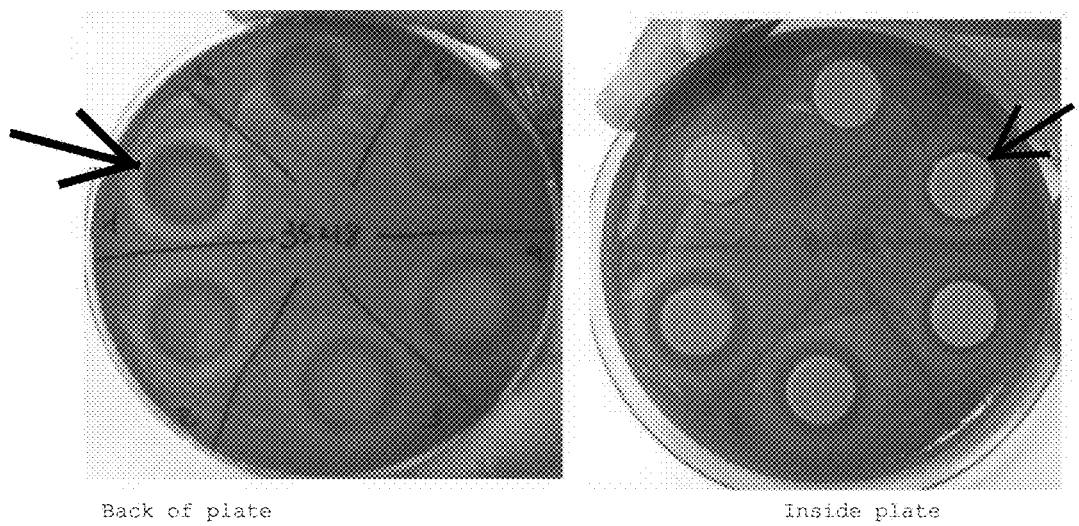
FIG. 4 reports the results of inhibition haloes expressed in millimetres of the following six probiotic strains against *Escherichia coli* ATCC 35218. The results are, starting from the arrow in a clockwise direction in the left panel and in a counter-clockwise direction in the right panel:
1. *L. reuteri* DLLRE08, DSM 25684 4mm
2. *L. reuteri* ID 1774 LRE 02, DSM 23878 2mm
3. *L. reuteri* DSM 17938 (Positive ref.) 5mm
4. *L. plantarum* LP01 LMG P-21021 5mm
5. *L. delbr.* susp. *bulgaricus* LDD01 2mm
6. *L. pentosus* PCB 101 1mm The left panel represents a back of plate view and the right panel represents an inside plate view. The arrow points to No. 1 in both the back of plate view and inside plate view.

6.1 For *Listeria monocytogenes* ATCC 19112, the results are given in FIG. 1.
   FIG. 1 shows:
   Probiotic strains mm:
   1. *L. reuteri* DLLRE08, DSM 25684 0 mm
   2. *L. reuteri* ID 1774 LRE 02, DSM 23878 0 mm
   3. *L. reuteri* DSM 17938 (Positive ref.) 0 mm
   4. *L. plantarum* LP01 LMG P-21021 5 mm
   5. *L. delbr.* susp. *bulgaricus* LDD01 2 mm
   6. *L. pentosus* PCB 101 4 mm 6.2 For *Enterococcus* sp. (from infant faeces), the results are given in FIG. 2.
   FIG. 2 shows (back of plate: in a clockwise direction starting from #1, the arrow points to #1) (inside plate: in a counter-clockwise direction starting from #1, the arrow points to #1):
   Probiotic strains mm:
   1. *L. reuteri* DLLRE08, DSM 25684
   2. *L. reuteri* ID 1774 LRE 02, DSM 23878
   3. *L. reuteri* DSM 17938 (Positive ref.)
   4. *L. plantarum* LP01 LMG P-21021
   5. *L. delbr.* susp. *bulgaricus* LDD01
   6. *L. pentosus* PCB 101
   Results: Inhibition haloes expressed in millimetres
   Probiotic strains mm:
   1. *L. reuteri* DLLRE08, DSM 25684 3 mm
   2. *L. reuteri* ID 1774 LRE 02, DSM 23878 3 mm
   3. *L. reuteri* DSM 17938 (Positive ref.) 3 mm
   4. *L. plantarum* LP01 LMG P-21021 5 mm
   5. *L. delbr.* susp. *bulgaricus* LDD01 4 mm
   6. *L. pentosus* PCB 101 2 mm 6.3 For *Escherichia coli* ATCC 8739, the results are given in FIG. 3.
   FIG. 3 shows (back of plate: in a clockwise direction starting from #1, the arrow points to #1) (inside plate: in a counter-clockwise direction starting from #1, the arrow points to #1):
   Probiotic strains mm:
   1. *L. reuteri* DLLRE08, DSM 25684
   2. *L. reuteri* ID 1774 LRE 02, DSM 23878
   3. *L. reuteri* DSM 17938 (Positive ref.)
   4. *L. plantarum* LP01 LMG P-21021
   5. *L. delbr.* susp. *bulgaricus* LDD01
   6. *L. pentosus* PCB 101
   Results: Inhibition haloes expressed in millimetres
   Probiotic strains mm:
   1. *L. reuteri* DLLRE08, DSM 25684 0 mm
   2. *L. reuteri* ID 1774 LRE 02, DSM 23878 1 mm
   3. *L. reuteri* DSM 17938 (Positive ref.) 2 mm
   4. *L. plantarum* LP01 LMG P-21021 4 mm
   5. *L. delbr.* susp. *bulgaricus* LDD01 2 mm
   6. *L. pentosus* PCB 101 1 mm 6.4 For *Escherichia coli* ATCC 35218, the results are given in FIG. 4.
   FIG. 4 shows (back of plate: in a clockwise direction starting from #1, the arrow points to #1) (inside plate: in a counter-clockwise direction starting from #1, the arrow points to #1):
   Probiotic strains mm:
   1. *L. reuteri* DLLRE08, DSM 25684
   2. *L. reuteri* ID 1774 LRE 02, DSM 23878
   3. *L. reuteri* DSM 17938 (Positive ref.)
   4. *L. plantarum* LP01 LMG P-21021
   5. *L. delbr.* susp. *bulgaricus* LDD01
   6. *L. pentosus* PCB 101
   Results: Inhibition haloes expressed in millimetres
   Probiotic strains mm:
   1. *L. reuteri* DLLRE08, DSM 25684 4 mm
   2. *L. reuteri* ID 1774 LRE 02, DSM 23878 2 mm
   3. *L. reuteri* DSM 17938 (Positive ref.) 5 mm
   4. *L. plantarum* LP01 LMG P-21021 5 mm
   5. *L. delbr.* susp. *bulgaricus* LDD01 2 mm
   6. *L. pentosus* PCB 101 1 mm 6.5 For *Klebsiella* sp (from infant faeces), the results are given in FIG. 5.

Figure 5:
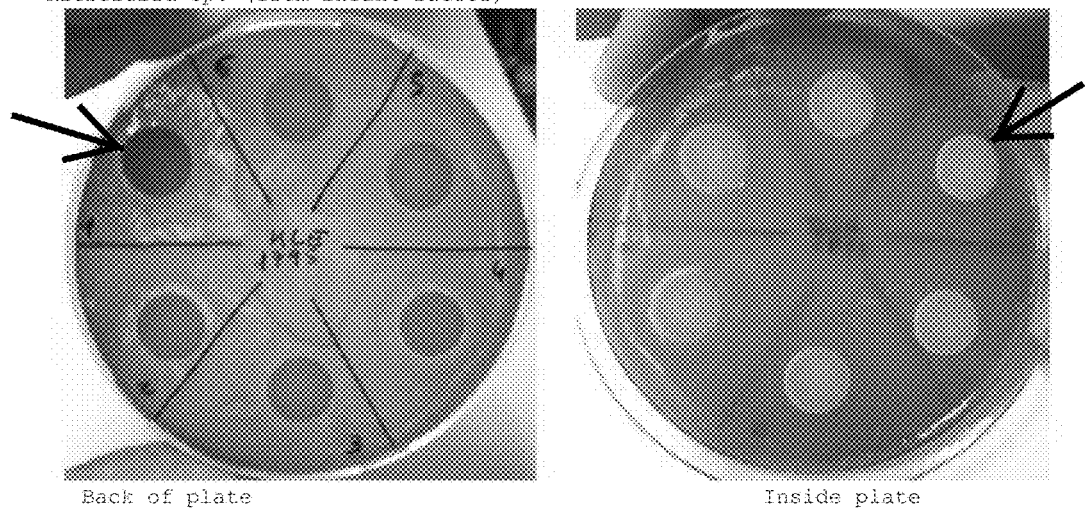
FIG. 5 reports the results of inhibition haloes expressed in millimetres of the following six probiotic strains against *Klebsiella* sp. (from infant faeces). The results are, starting from the arrow in a clockwise direction in the left panel and in a counter-clockwise direction in the right panel:
1. *L. reuteri* DLLRE08, DSM 25684 0mm
2. *L. reuteri* ID 1774 LRE 02, DSM 23878 2mm
3. *L. reuteri* DSM 17938 (Positive ref.) 2mm
4. *L. plantarum* LP01 LMG P-21021 3mm
5. *L. delbr.* susp. *bulgaricus* LDD01 1mm
6. *L. pentosus* PCB 101 0mm The left panel represents a back of plate view and the right panel represents an inside plate view. The arrow points to No. 1 in both the back of plate view and inside plate view.

FIG. 5 shows (back of plate: in a clockwise direction starting from #1, the arrow points to #1) (inside plate: in a counter-clockwise direction starting from #1, the arrow points to #1):
Probiotic strains mm:
1. L. reuteri DLLRE08, DSM 25684
2. L. reuteri ID 1774 LRE 02, DSM 23878
3. L. reuteri DSM 17938 (Positive ref.)
4. L. plantarum LP01 LMG P-21021
5. L. delbr. susp. bulgaricus LDD01
6. L. pentosus PCB 101
Results: Inhibition haloes expressed in millimetres
Probiotic strains mm:
1. L. reuteri DLLRE08, DSM 25684 0 mm
2. L. reuteri ID 1774 LRE 02, DSM 23878 2 mm
3. L. reuteri DSM 17938 (Positive ref.) 2 mm
4. L. plantarum LP01 LMG P-21021 3 mm
5. L. delbr. susp. bulgaricus LDD01 1 mm
6. L. pentosus PCB 101 0 mm

The invention claimed is:

1. A method for treatment of colic, diarrhea and intestinal disorders in a subject of pediatric age, the method comprising:
   administering to the subject an effective amount of a food composition or supplement product or pharmaceutical composition,
   the food composition or supplement product or pharmaceutical composition comprising a bacterial mixture, said bacterial mixture comprising at least one viable bacterial strain belonging to the species *Bifidobacterium breve*, and a bacterial strain belonging to the species *Bifidobacterium longum* or *Bifidobacterium longum* subsp. *longum* the bacterial mixture having an antimicrobial activity against the pathogens *E. coli, Salmonella enteriditis, Clostridium difficile* and *Campylobacter jejunii*,
   wherein the at least one viable bacterial strain belonging to the species *Bifidobacterium breve* comprises *Bifidobacterium breve* B632, deposited by the company Probiotical SpA of Novara (Italy) with the Depositary Institution DSMZ on Apr. 7, 2011 and having the deposit number DSM 24706.

2. The method according to claim 1, wherein the at least one bacterial strain further comprises a bacterial strain belonging to the species *Bifidobacterium breve* selected from the group consisting of
   *Bifidobacterium breve* B2274, deposited by the company Probiotical SpA of Novara (Italy) with the Depositary Institution DSMZ on Apr. 7, 2011 and having the deposit number DSM 24707;
   *Bifidobacterium breve* B7840, deposited by the company Probiotical SpA of Novara, (Italy) with the Depositary Institution DSMZ on Apr. 7, 2011 and having the deposit number DSM 24708; and
   *Bifidobacterium breve* BR03, deposited by the company Probiotical SpA of Novara (Italy) with the Depositary Institution DSMZ and having the deposit number DSM 16604.

3. The method according to claim 1, wherein the strain belonging to the species *Bifidobacterium longum* is *Bifidobacterium longum* subsp. *longum* B1975, deposited by the company Probiotical SpA of Novara (Italy) with the Depositary Institution DSMZ on Apr. 7, 2011 and having the deposit number DSM 24709.

4. The method according to claim 1, wherein the at least one bacterial strain further comprises *Bifidobacterium breve* BR03, deposited by the company Probiotical SpA of Novara (Italy) with the Depositary Institution DSMZ and having the deposit number DSM 16604.

5. The method according to claim 1, wherein the bacterial mixture further comprises *Bifidobacterium breve* BR03, deposited by the company Probiotical SpA of Novara (Italy) with the Depositary Institution DSMZ and having the deposit number DSM 16604, in association with *Lactobacillus plantarum* LPOI deposited by the company Mofin Srl of Novara (Italy) with the Depositary Institution BCCM-LMG on Oct. 16, 2001 and having the deposit number LMG P-21021.

6. The method according to claim 1, wherein the food composition or supplement product or pharmaceutical composition comprising a bacterial mixture is added or suspended in a vegetable oil selected from among olive oil, corn oil, sunflower oil, seed oil and palm oil.

7. The method according to claim 6, wherein the food composition or supplement product or pharmaceutical composition is a composition comprising at least one vegetable substance selected from the group comprising of sterols or phytosterols, stanols or phytostanols, glucomannan, konjac gum and/or at least one prebiotic fibre selected from the group comprising fructo-oligosaccharides FOS, galacto-oligosaccharides -GOS, xylo-oligosaccharides -XOS, inulin, larch fibre or arabinogalactan and/or fermented red rice and/or betaglucans from oats, oat bran, barley, barley bran and/or aloe arborescens gel in lyophilized form.

8. The method for the treatment of colic, diarrhea and intestinal disorders in subjects of pediatric age according to claim 6, wherein the said food composition or supplement product or pharmaceutical composition is a composition comprising simethicone.

9. The method according to claim 1, wherein the at least one bacterial strain further comprises
   *Bifidobacterium breve* B2274, deposited by the company Probiotical SpA of Novara (Italy) with the Depositary Institution DSMZ on Apr. 7, 2011 and having the deposit number DSM 24707,
   *Bifidobacterium breve* B7840, deposited by the company Probiotical SpA of Novara, (Italy) with the Depositary Institution DSMZ on Apr. 7, 2011 and having the deposit number DSM 24708; and
   *Bifidobacterium longum* subsp. *longum* B1975, deposited by the company Probiotical SpA of Novara (Italy) with the Depositary Institution DSMZ on Apr. 7, 2011 and having the deposit number DSM 24709.

* * * * *